US009248172B2

(12) United States Patent
Srivastava et al.

(10) Patent No.: US 9,248,172 B2
(45) Date of Patent: *Feb. 2, 2016

(54) USING HEAT SHOCK PROTEINS TO IMPROVE THE THERAPEUTIC BENEFIT OF A NON-VACCINE TREATMENT MODALITY

(71) Applicant: University of Connecticut Health Center, Farmington, CT (US)

(72) Inventors: Pramod K. Srivastava, Avon, CT (US); Zihai Li, Mount Pleasant, SC (US)

(73) Assignee: University of Connecticut Health Center, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/043,666

(22) Filed: Oct. 1, 2013

(65) Prior Publication Data

US 2014/0107391 A1    Apr. 17, 2014

Related U.S. Application Data

(60) Continuation of application No. 13/250,141, filed on Sep. 30, 2011, now Pat. No. 8,591,890, which is a division of application No. 12/418,724, filed on Apr. 6, 2009, now Pat. No. 8,029,808, which is a division of application No. 11/283,103, filed on Nov. 18, 2005, now abandoned, which is a division of application No. 10/322,312, filed on Dec. 16, 2002, now Pat. No. 6,984,389, which is a continuation-in-part of application No. 10/131,961, filed on Apr. 25, 2002, now abandoned.

(51) Int. Cl.
| | | |
|---|---|---|
| A61K 39/00 | (2006.01) |
| A61K 39/395 | (2006.01) |
| A61N 5/10 | (2006.01) |
| A61K 31/7048 | (2006.01) |
| A61K 45/06 | (2006.01) |
| A61K 38/17 | (2006.01) |
| A61K 38/20 | (2006.01) |
| A61K 31/135 | (2006.01) |
| A61K 31/196 | (2006.01) |
| A61K 31/277 | (2006.01) |
| A61K 31/353 | (2006.01) |
| A61K 31/395 | (2006.01) |
| A61K 31/506 | (2006.01) |
| A61K 31/675 | (2006.01) |

(52) U.S. Cl.
CPC ........... *A61K 39/0011* (2013.01); *A61K 31/135* (2013.01); *A61K 31/196* (2013.01); *A61K 31/277* (2013.01); *A61K 31/353* (2013.01); *A61K 31/395* (2013.01); *A61K 31/506* (2013.01); *A61K 31/675* (2013.01); *A61K 31/7048* (2013.01); *A61K 38/1709* (2013.01); *A61K 38/208* (2013.01); *A61K 39/39558* (2013.01); *A61K 45/06* (2013.01); *A61N 5/10* (2013.01); *A61K 2039/6043* (2013.01)

(58) Field of Classification Search
None
See application file for complete search history.

(56) References Cited

U.S. PATENT DOCUMENTS

| | | | |
|---|---|---|---|
| 5,580,859 A | 12/1996 | Felgner et al. |
| 5,736,146 A | 4/1998 | Cohen |
| 5,750,119 A | 5/1998 | Srivastava |
| 5,830,464 A | 11/1998 | Srivastava |
| 5,837,251 A | 11/1998 | Srivastava |
| 5,869,058 A | 2/1999 | Cohen |
| 5,935,576 A | 8/1999 | Srivastava |
| 5,939,098 A | 8/1999 | Reidenberg et al. |
| 5,961,979 A | 10/1999 | Srivastava |
| 5,985,270 A | 11/1999 | Srivastava |
| 5,997,873 A | 12/1999 | Srivastava |
| 6,017,540 A | 1/2000 | Srivastava |
| 6,030,618 A | 2/2000 | Srivastava |
| 6,048,530 A | 4/2000 | Srivastava |
| 6,136,315 A | 10/2000 | Srivastava |
| 6,251,886 B1 | 6/2001 | Friedman |
| 6,316,462 B1 | 11/2001 | Bishop et al. |
| 6,984,389 B2 | 1/2006 | Li |
| 7,132,109 B1 | 11/2006 | Srivastava |
| 7,446,124 B2 | 11/2008 | Kirkpatrick et al. |
| 8,029,808 B2 | 10/2011 | Srivastava et al. |

(Continued)

FOREIGN PATENT DOCUMENTS

| | | |
|---|---|---|
| FR | 2835746 | 8/2003 |
| RU | 2154646 C2 | 8/2000 |

(Continued)

OTHER PUBLICATIONS

U.S. Appl. No. 10/131,961, filed May 1, 2003, Srivastava.

(Continued)

*Primary Examiner* — Karen Canella
(74) *Attorney, Agent, or Firm* — Wolf, Greenfield & Sacks, P.C.

(57) ABSTRACT

The present invention relates to methods of improving a treatment outcome comprising administering a heat shock protein (HSP) preparation or an α-2-macroglobulin (α2M) preparation with a non-vaccine treatment modality. In particular, an HSP preparation or an α2M preparation is administered in conjunction with a non-vaccine treatment modality for the treatment of cancer or infectious diseases. In the practice of the invention, a preparation comprising HSPs such as but not limited to, hsp70, hsp90 and gp96 alone or in combination with each other, noncovalently or covalently bound to antigenic molecules or α2M, noncovalently or covalently bound to antigenic molecules is administered in conjunction with a non-vaccine treatment modality.

20 Claims, 1 Drawing Sheet

(56) References Cited

U.S. PATENT DOCUMENTS

| | | | |
|---|---|---|---|
| 8,591,890 | B2 | 11/2013 | Srivastava et al. |
| 2002/0037290 | A1 | 3/2002 | Armen |
| 2002/0172682 | A1 | 11/2002 | Srivastava |
| 2002/0192230 | A1 | 12/2002 | Srivastava |
| 2004/0022796 | A1 | 2/2004 | Srivastava |
| 2004/0253228 | A1 | 12/2004 | Srivastava |
| 2005/0221395 | A1 | 10/2005 | Zabrecky et al. |
| 2006/0079458 | A1 | 4/2006 | Srivastava et al. |
| 2006/0093612 | A1 | 5/2006 | Srivastava |
| 2012/0021997 | A1 | 1/2012 | Srivastava et al. |

FOREIGN PATENT DOCUMENTS

| | | |
|---|---|---|
| WO | WO 94/14976 | 7/1994 |
| WO | WO 95/34638 | 12/1995 |
| WO | WO 97/06821 | 2/1997 |
| WO | WO 98/34641 | 8/1998 |
| WO | WO 99/09030 | 2/1999 |
| WO | WO 99/49881 | 10/1999 |
| WO | WO 99/50303 | 10/1999 |
| WO | WO 99/60142 | 11/1999 |
| WO | WO 00/54801 | 9/2000 |
| WO | WO 00/54839 | 9/2000 |
| WO | WO 01/34607 | 5/2001 |
| WO | WO 01/91787 | 6/2001 |
| WO | WO 01/77107 | 10/2001 |
| WO | WO 02/11669 | 2/2002 |
| WO | WO 02/22133 | 2/2002 |
| WO | WO 02/18608 | 3/2002 |
| WO | WO 02/32923 | 4/2002 |
| WO | WO 02/34205 | 5/2002 |
| WO | WO 03/092624 | 5/2003 |

OTHER PUBLICATIONS

U.S. Appl. No. 10/131,937, filed Apr. 25, 2002, Srivastava.
U.S. Appl. No. 10/126,368, filed Apr. 19, 2002, Srivastava.
U.S. Appl. No. 09/693,643, filed Oct. 20, 2000, Srivastava.
U.S. Appl. No. 60/223,133, filed Sep. 18, 2000, Armen.
U.S. Appl. No. 60/377,483, filed May 2, 2002, Srivastava.
U.S. Appl. No. 60/377,484, filed May 20, 2002, Srivastava.
[No Author Listed] Updated Phase 2 Data of Prophage in Newly Diagnosed GBM Presented at ASCO Show Improvement in Median Progression Free Survival and Overall Survival Independently of Prognostic Markers, Compared with Historical Expectations. Agenus Bio Investor Center. Jun. 1, 2015. Retrieved from http://investor.agenusbio.com/press-release/updated-phase-2-data-prophage-newly-diagnosed-gbm-presented-ascoshow-improvement-medi on Jul. 10, 2015.
[No Author Listed] Agenus Announces Oral Presentation at ASCO Highlighting Improved Survival with Prophage Immunotherapy in Brain Cancer Compared to Historical Controls. Agenus Bio Investor Center. May 14, 2015. Retrieved from http://investor.agenusbio.com/press-release/agenus-announces-oral-presentation-asco-highlighting-improved-survivalprophage-Immune on Jul. 10, 2015.
[No Author Listed] Agenus Brain Cancer Vaccine Shows Extended Survival in Phase 2 Final Data Analysis. Agenus Bio Investor Center. Jul. 1, 2014. Retrieved from http://investor.agenusbio.com/press-release/agenus-brain-cancer-vaccine-shows-extended-survival-phase-2-finaldata- Analysis on Jul. 10, 2015.
[No Author Listed] Agenus' Prophage Vaccine for Glioma Hailed As a 'Very Promising Therapy' in an Editorial Published in the Journal Neuro-Oncology. Agenus Bio Investor Center. Jan. 21, 2014. Retrieved from http://investor.agenusbio.com/press-release/agenus-prophage-vaccine-glioma-hailed-very-promising-therapy-editorialpublished-Journ on Jul. 10, 2015.
[No Author Listed] Agenus Announces Phase 2 Checkpoint inhibitor Combination Trial with Prophage Cancer Vaccine for Melanoma. Agenus Bio Investor Center. Jan. 14, 2014. Retrieved from http://investor.agenusbio.com/press-release/agenus-announces-phase-2-checkpoint-inhibitor-combination-trialprophage-cancer-vaccin on Jul. 10, 2015.

[No Author Listed] Positive Phase 2 Results from Agenus' Brain Cancer Vaccine Published in Neuro-Oncology. Agenus Bio Investor Center. Dec. 16, 2013. Retrieved from http://investor.agenusbio.com/press-release/positive-phase-2-results-agenus-brain-cancer-vaccine-publishedin%C2%A0neuro-oncology on Jul. 10, 2015.
[No Author Listed] Agenus' Brain Cancer Vaccine Program Named a "Top Project to Watch" by Elsevier Business Intelligence. Agenus Bio Investor Center. Nov. 18, 2013. Retrieved from URL: http://investor.agenusbio.com/press-release/agenus-brain-cancer-vaccine-program-named-top-project-watch-elsevierbusiness-Intellig on Jul. 10, 2015.
[No Author Listed] Agenus Reports Third Quarter 2013 Financial Results. Agenus Bio Investor Center. Oct. 24, 2013. Retrieved from http://investor.agenusbio.com/press-release/earnings/agenus-reports-third-quarter-2013-financial-results on Jul. 10, 2015.
[No Author Listed] Agenus Reports Positive Follow-on Phase 2 Results for Brain Cancer Vaccine in Newly Diagnosed Patients. Agenus Bio Investor Center. Sep. 17, 2013. Retrieved from http://investor.agenusbio.com/press-release/agenus-reports-positive-follow-phase-2-results-brain-cancer-vaccinenewly-diagnosed-pa on Jul. 10, 2015.
[No Author Listed] Agenus Announces Initiation of Enrollment in NCISponsored Randomized Trial of Prophage G-200 Vaccine with Avastin in Treatment of Brain Tumors. Agenus Bio Investor Center. May 22, 2013. Retrieved from http://investor.agenusbio.com/press-release/agenus-announces-initiation-enrollment-nci-sponsored-randomized-trialprophage-g-200-v on Jul. 10, 2015.
[No Author Listed] Agenus Reports First Quarter 2011 Financial Results. Exhibit 99.1. Apr. 28, 2011. Last accessed at http://www.sec.gov/archives/edgar/data/1098972/000117184311001163/newsrelease.htm on Dec. 4, 2013.
[No Author Listed] Chemotherapy wafer implants (Gliadel wafers). Cancer Research UK. Dec. 4, 2012. Last accessed at http://www.cancerresearchuk.org/cancer-help/about-cancer/cancer-questions/chemotherapy-wafer-implants on Dec. 4, 2013.
[No Author Listed] New treatment protocol at westchester brain tumor program offers a ray of hope for deadly cancer. Westchester Brain Tumor Program. PRLOG Press Release Distribution. Dec. 15, 2011. Last accessed at http://www.prlog.org/11750761-new-treatment-protocol-at-westchester-brain-tumor-program-offers-ray-of-hope-for-deadly-cancer.html on Dec. 4, 2013.
[No Author Listed], Agenus Inc. conference corporate presentation. Mar. 9, 2011.
[No Author Listed], HSPPC-96 Vaccine may offer benefit for glioblastoma multiforme patients. American Association of Neurological Surgeons. Apr. 9, 2012. Last accessed at http://newswise.com/articles/view/587846?print-article on Dec. 5, 2013.
[No Author listed], Biologic Therapy of Cancer, J.B. (de Vita et al., ed., J.B. Lippincott Company, Philadelphia, PA 1995) pp. 668-689 and 803-816.
[No Author Listed], Jordan Report, 2002. Division of Microbiology and Infectious Diseases, National Institute of Allergy and Infectious Diseases, National Institutes of Health, United States.
[No Author listed], NLM Gateway Concept, downloaded from the Web Mar. 16, 2008.
[No Author Listed], Roche announces final phase III study results of Avastin plus radiotherapy and chemotherapy in people with an aggressive form of brain cancer. Roche Media Release. Jun. 1, 2013; 1-5.
[No Author Listed], Roche's Avastin approved in Japan for treatment of the most aggressive form of brain cancer. Roche Media Release. Jun. 17, 2013;1-4.
[Not Author listed], Chronic Myeloid Leukemia Trialists' Collaborative Group, 1997, J. Natl. Cancer Inst. 89(2):1616-1620.
Adams et al, New agents in cancer clinical trials, Oncogene (2000) 19:6687-6692.
Almand et al. 2001, Increased production of immature myeloid cells in cancer patients: a mechanism of immunosuppression in cancer, J. Immunol. 166(1):678-689.
Ampie et al., Heat shock protein vaccines against glioblastoma: from bench to bedside. J Neurooncol. Jul. 2015;123(3):441-448. Epub Jun. 21, 2015.

(56) References Cited

OTHER PUBLICATIONS

Anderson et al., 1994, Effective vaccination of mice against *Mycobacterium tuberculosis* infection with a soluble mixture of secreted mycobacterial proteins, Infect. Immun. 62(6):2536-2544.
Anthony et al. 1999, Priming of CD8+ CTL effector cells in mice by immunization with a stress protein-influenza virus nucleoprotein fusion molecules, Vaccine 17(4):373-383.
Armstrong et al., Comparative impact of treatment on patient reported outcomes (PROs) in patients with glioblastoma (GBM) enrolled in RTOG 0825. J Clin Oncol. 2013;31. Abstract 2003.
Asea et al 2000 HSP70 stimulates cytokine production through a CD14-dependant pathway, demonstrating its dual role as a chaperone and cytokine, Nature Medicine 6:435-442.
Banchereau et al 1998 Dendritic cells and the control of immunity Nature 392:245-252.
Barbour et al. 2001, Imatinib for chronic myeloid leukemia: a NICE mess, The Lancet, Lancet Limited, London, GB vol. 358(9292), p. 1478.
Barnes, Agenus announces intiation of enrollment in nci-sponsored randomized trial of prophage g-200 vaccine with avastin in treatment of brain tumors. May 22, 2013.
Barnes, Positive phase 2 data from agenus' brain cancer vaccine presented at plenary session of american academy of neurological surgeons meeting. May 1, 2013.
Barrios et al. 1992, Mycobacterial heat-shock proteins as carrier molecules II: The use of the 70-kDa mycobacterial heat-shock protein as carrier for conjugated vaccines can circumvent the need for adjuvants and Bacillus Calmette Guerin priming, Eur. J. Immunol. 22(6):1365-1372.
Barrios et al. 1994 Heat shock proteins as carrier molecules: in vivo helper effect mediated by *Escherichia coli* GroEL and DNA K proteins requires cross-linking with antigen, Clin, Exp Immunol. 98(2):229-233.
Basu et al. 1999, Calreticulin, a peptide-binding chaperone of the endoplasmic reticulum, elicits tumor- and peptide-specific immunity, J. Exp Med. 189(5):797-802.
Basu et al. 2000, Necrotic but not apoptotic cell death releases heat shock proteins, which deliver a partial maturation signal to dendritic cells and activate the NF-kappa B pathway, Int. Immunol. 12(11):1539-1546.
Basu et al., 2001 CD91 is a common receptor for heat shock proteins gp96, hsp90, hsp70, and calreticulin, Immunity 14(3):303-313.
Becker, Rethinking immunotherapy for brain tumors. Seeking Alpha. Feb. 24, 2012. Last accessed at http://seekingalpha.com/article/391521-rethinking-immunotherapy-for-brain-tumors on Dec. 4, 2013.
Berke et al 2000, Peptide spanning the junctional region of both the abl/bcr and the bcr/abl proteins bind common HLA class 1 molecules, Leukemia 14:419-426.
Bettelheim et al., Introduction of General Organic and Biochemistry $2^{nd}$ ed. W.B. Saunders Company, New York, NY 1988, Chapter 11, p. 270-299.
Binder et al. 2000, CD91: a receptor for heat shock protein gp96, Nat. Immunol. 1(2):151-155.
Binder et al. 2001, Adjuvanticity of alpha 2-macroglubolin an independent ligand for the heat shock protein receptor CD91, J. Immunol. 166(8):4968-4972.
Birkenmeier, G. 2001, Targeting the Proteinase Inhibitor and Immune Modulatory Function of Human α2-Macroglobulin, Mod. Asp. Immunobiol. 2(1):32-36.
Blachere et al. 1997, Heat shock protein-peptide complexes, reconstituted in vitro, elicit peptide-specific cytotoxic T lymphocyte response and tumor immunity, J. Exp. Med. 186(8):1315-1322.
Blander et al 1993, Major cytoplasmic membrane protein of Legionella pneumophila, a genus common antigen and member of the hsp 60 family of heat shock proteins, induces protective immunity of a guinea pig model of Legionnairs disease. J. Clin. Invest. 91(2):717-723.

Bloch et al., Impact of extent of resection for recurrent glioblastoma on overall survival:clinical article. J Neurosurg. Dec. 2012;117(6):1032-8. doi:10.3171/2012.9.JNS12504. Epub Oct. 5, 2012.
Bortin et al., 1987, HLA Associations with Leukemia, Blood 70(1): 227-232.
Breoler et al., 1999 In vivo and in vitro activation of T cells after administration of Ag-negative heat shock proteins, J. Immunol. 162:3141-3147.
Buchdunger et al., Pharmacology of imatinib (STI571). Eur J Cancer. Sep. 2002;38 Suppl 5:S28-36.
Carlo-Stella et al. Selection of myeloid progenitors lacking BCR/ABL mRNA in chronic myelogenous leukemia patients after in vitro treatment with the tyrosine kinase inhibitor genistein, Blood 1996, vol. 88, pp. 3091-3100.
Castaigne et al., Blood 1990, vol. 76, pp. 1704-1709.
Chambault-Guerin et al., 2000, Effects of retinoic acid and tumor necrosis factor alpha on GL-15 glioblastoma cells, Neuroreport vol. 11(2):389-393.
Chen et al. 1999, Human 60-kDa heat-shock protein: a danger signal to the innate immune system. J. Immunol. 162:3212-3219.
Chen et al. 2000, Enhancement of DNA vaccine potency by linkage of antigen gene to an HSP70 gene, Cancer Res. 60:1035-1042.
Chinot et al., Bevacizumab plus radiotherapy-temozolomide for newly diagnosed glioblastoma. N Engl J Med. Feb. 20, 2014;370(8):709-22. doi: 10.1056/NEJMoa1308345.
Chu et al. 1993, Receptor-mediated antigen delivery into macrophages: Complexing antigen to alpha 2-macroglobulin enhances presentation to T cells, J. Immunol. 150(1):48-58.
Chu et al. 1994, Alpha 2-macroglobulin, complement, and biologic defense: antigens, growth factors, microbial proteases, and receptor ligation, Lab. Invest. 71(6):792-812.
Chu et al. 1994, Alpha 2-macroglobulin: a sensor for proteolysis, Ann. NY Acad. Sci 737:291-307.
Chu et al., 1994, Adjuvant-fre in vivo targeting: Antigen delivery by alpha 2-macroglobulin enhances antibody formation, J. Immunol 152(4):1538-1545.
Craig et al. 1993, Chaperones: helpers along the pathways to protein folding, Scinece 260:1902-1903.
Crane et al., Individual patient-specific immunity against high-grade glioma after vaccination with autologous tumor derived peptides bound to the 96 KD chaperone protein. Clin Cancer Res. Aug. 7, 2012. [Epub ahead of print].
Curley et al., 1995, Identification and screening of 416 patients with chronic hepatitis at high risk to develop hepatocellular cancer. Ann. Surg. 222(3):375-383.
Dazzi et al. 1999, Donor lymphocyte infusions for relapse of chronic myeloid leukemia after allogenic stem cell transplant: Where we now stand, Experimental Hematology 27:1477-1486.
Del Giudice et al., 1994, Hsp70: a carrier molecule with built-in adjuvanticity, Experientia 50(11-12):1061-1066.
Dorak et al., 1994, Human Major Histocompatibility Complex Contains Several Leukemia Susceptibility Genes, Leukemia and Lymphoma 12:211-222.
Drucker et al., 2000, Lessons learned from the development of an abl tyrosine kinase inhibitor for chronic myelogenous leukemia, J. Clin. Invest. 105(1):3-7.
Druker et al., 2001, Activity of a specific inhibitor of the BCR-ABL tyrosine kinase in the blast crisis of chronic myeloid leukemia and acute lymphoblastic leukemia with the Philadelphia chromosome, New England J. Med. 344(14):1038-1042.
Druker et al., 2001, Efficacy and safety of a specific inhibitor of the BCR-ABL tyrosine kinase in chronic myeloid leukemia, New England J. Med. 344(14):1031-1037.
Ebos et al., Imatinib mesylate (STI-571) reduces Bcr-Abl-mediated vascular endothelial growth factor secretion in chronic myelogenous leukemia. Mol Cancer Res. Dec. 2002;1(2):89-95.
Egilman et al., 1996, Lung cancer and asbestos exposure: asbestosis is not necessary, Am. J. Ind. Med. 30(4):398-406.
Elwood, 1992, Melanoma and sun exposure: contrasts between intermittent and chronic exposure, World J. Surg. 16(2):157-165.
Evans et al., 1999, Vaccine therapy for cancer—fact or fiction? QJM 92(6):299-307.

(56) References Cited

OTHER PUBLICATIONS

Faderl et al., 1999, The biology of chronic myeloid leukemia, New England J. Med. 341(3):164-172.

Feng et al., 2002, Exogenous heat shock proteins provide adjuvant effects on enhancing the immunogenicity of apoptotic tumor cells and inducing antitumor immunity, AACR 93.sup.rd Annual Meeting, vol. 43, Abstract # 2214.

Ferrero et al., 1995, The GroES homolog of Helicobacter pylori confers protective immunity against mucosal infection in mice, Proc. Natl. Acad. Sci. USA 92(14):6499-6503.

Finlay et al., Activating mutations for transformation by p53 produce a gene product that forms an hsc70-p53 complex with an altered half-life. Mol Cell Biol. Feb. 1988;8(2):531-9.

Gabrilovich et al., Antibodies to vascular endothelial growth factor enhance the efficacy of cancer immunotherapy by improving endogenous dendritic cell function. Clin Cancer Res. Oct. 1999;5(10):2963-70.

Gabrilovich et al., Production of vascular endothelial growth factor by human tumors inhibits the functional maturation of dendritic cells. Nat Med. Oct. 1996;2(10):1096-103.

Gallucci et al., 1999, Natural adjuvants: endogenous activators of dendritic cells, Nat. Med. 5:1249-1255.

Gelber et al., 1992, Vaccination of mice with a soluble protein fraction of *Mycobacterium leprae* provides consistent and long-term protection against *M. leprae* infection, Infect. Immun. 60(5):1840-1844.

Gelber et al., 1994, Vaccination with pure *Mycobacterium leprae* proteins inhibits *M. leprae* multiplication in mouse footpads, Infect. Immun. 62(10):4250-4255.

Gething et al., 1992, Protein folding in the cell, Nature 355:33-45.

Gilbert et al., RTOG 0825: Phase III double-blind placebo-controlled trial evaluating bevacizumab (Bev) in patients (Pts) with newly diagnosed glioblastoma (GBM). J Clin Oncol. 2013;31. Abstract 01.

Gilbert et al., A randomized trial of bevacizumab for newly diagnosed glioblastoma. N Engl J Med. Feb. 20, 2014;370(8):699-708. doi:10.1056/NEJMoa1308573.

Gomez et al., 1991, Protective efficacy of a 62-kilodalton antigen, HIS-62, from the cell wall and cell membrane of Histoplasma capsulatum yeast cells, Infect. Immun. 59(12):4459-4464.

Gomez et al., 1992, An 80-kilodalton antigen from Histoplasma capsulatum that has homology to heat shock protein 70 induces cell-mediated immune responses and protection in mice, Infect. Immun. 60(7):2565-2571.

Gomez et al., 1995, Vaccination with recombinant heat shock protein 60 from Histoplasma capsulatum protects mice against pulmonary histoplasmosis, Infect. Immun. 63(7):2587-2595.

Graner et al., 2003, Tumor-derived chaperone-rich cell lysates are effective therapeutic vaccines against a variety of cancers, Cancer Immunol. Immunother. 52(4)226-234.

Haas et al., 1983, Immunoglobulin heavy chain binding protein, Nature 306(5941):387-389.

Haas et al., 1992, Parental Origin of Chromosomes Involved in the Translocation t(9,22), Nature 359 (1):414-416.

Hall et al., 1981, Proteolytic cleavage sites on alpha 2-macroglobulin resulting in proteinase binding are different for trypsin and *Staphylococcus aureus* V-8 proteinase, Biochem Biophys Res Commun. 100(1):8-16.

Harris, New therapies improving survival in patients with glioblastoma. HemOnc Today. Jan. 25, 2010. Last accessed at http://www.healio.com/hematology-oncology/neuro-oncology/news/print/hematology-oncology/%7B11c4aa87-7f36-44e3-91d2-518da4cc0d6b%7D/new-therapies-improving-survival-in-patients-with-glioblastoma on Dec. 4, 2013.

Hebert et al., 1997, The number and location of glycans on influenza hemagglutinin determine folding and association with calnexin and calreticulin, J. Cell Biol. 139(3):613-623.

Henriksson et al., Progression-free survival (PFS) and health-related quality of life (HRQoL) in AVAglio, a phase III study of bevacizumab (Bv), temozolomide (T), and radiotherapy (RT) in newly diagnosed glioblastoma (GBM). J Clin Oncol. 2013;31. Abstract 2005.

Hickey et al., Cellular and vaccine therapeutic approaches for gliomas. J Transl Med. Oct. 14, 2010;8:100. doi: 10.1186/1479-5876-8-100.

Holtet et al., 1994, Receptor-binding domain of human alpha 2-macroglobulin. Expression, folding and biochemical characterization of a high-affinity recombinant derivative, FEBS Lett. 344(2-3):242-246.

Hoon et al., Suppressor cell activity in a randomized trial of patients receiving active specific immunotherapy with melanoma cell vaccine and low dosages of cyclophosphamide. Cancer Res. 1990 Sep 1;50(17):5358-64.

Hoover et al., 1990, Cyclophosphamide and abrogation of tumor-induced suppressor T cell activity, Cancer Immunology, Immunotherapy:C:II 31 (2):121-127.

Horwitz et al., 1995, Protective immunity against tuberculosis induced by vaccination with major extracellular proteins of *Mycobacterium tuberculosis*, Proc. Natl. Acad. Sci. USA 92(5):1530-1534.

Hubbard et al., 1992, Immunization of mice with mycobacterial culture filtrate proteins, Clin. Exp. Immunol. 87(1):94-98.

Hwang et al. (abstract) PAACR, Mar. 2002, vol. 43, abstract No. 3909.

Inaba et al., 1992, Generation of large numbers of dendritic cells from mouse bone marrow cultures supplemented with granulocyte/macrophage colony-stimulating factor, J. Exp. Med. 176(6):1693-1702.

Jacob et al., 2002, Cytogenetic profile of chronic myeloid leukemias, Indian J. Cancer 39(2):61-65.

Janetzki et al., 2000, Immunization of cancer patients with autologous cancer-derived heat shock protein gp96 preparations: a pilot study, Int. J. Cancer 88(2):232-238.

Janeway et al., eds., 1997, Immuno Biology—The Immune System in Health and Disease, 3.sup.rd Ed., Chapter 6-7, Garland Publishing Inc. New York and London.

Kan et al., 1985, Nucleotide sequence of cDNA encoding human alpha 2-macroglobulin and assignment of the chromosomal locus, Proc. Natl. Acad. Sci. USA 82(8):2282-2286.

Kanamaru et al., Blood, 1995, vol. 85, pp. 1202-1206.

Kojima et al., 2002, Combination therapy of tumor-derived gp96 and GM-CSF or IL-12-gene transduced tumor cells in the control of LLC tumor, AACR 93.sup.rd Annual Meeting, vol. 43, Abstract #5516.

Kolialexi et al., 1998, Chromosome Fragility and Predisposition to Childhood Malignancies, Anticancer Research 18:2359-2364.

Kotera et al., Cancer Research, Nov. 15, 2001, vol. 61, pp. 8105-8109.

Kusmartsev et al., 2003, All-trans-retinoic acid eliminates immature myeloid cells from tumor-bearing mice and improves the effect of vaccination. Cancer Res. 63(15):4441-4449.

Kwon et al., 1999, Functions of newly identified members of the tumor necrosis factor receptor/ligand superfamilies in lymphocytes, Curr. Opin. Immunol. 11(3):340-345.

Lai et al., 1984, Quantitation and intracellular localization of the 85K heat shock protein by using monoclonal and polyclonal antibodies, Mol. Cell. Biol. 4:2802-2810.

Le Coutre et al., 2000, Induction of resistance to the Abelson inhibitor ST1571 in human leukemic cells through gene amplification, Blood 95(5):1758-1766.

Le et al., 2001, Pre-existing tumor-sensitized T cells are essential for eradication of established tumros by IL-12 and cyclophosphamide plus IL-12. J. Immunol. 167(12):6765-6772.

Li et al., Vascular endothelial growth factor blockade reduces intratumoral regulatory T cells and enhances the efficacy of a GM-CSF-secreting cancer immunotherapy. Clin Cancer Res. Nov. 15, 2006;12(22):6808-16.

Lindquist et al., 1988, The heat-shock proteins, Annu. Rev. Genetics 22:631-677.

Lodish et al., Molecular Cell Biology, 4th ed. W.H. Freeman and Company, New York, NY 2000. 20.1:849-858.

Lowrie et al., 1994, Towards a DNA vaccine against tuberculosis, Vaccine 12(16):1537-1540.

Lus Sow et al., 1991, Mycobacterial heat-shock proteins as carrier molecules, Eur. J. Immunol. 21(10):2297-2302.

(56) References Cited

OTHER PUBLICATIONS

Manning et al., A vascular endothelial growth factor receptor-2 inhibitor enhances antitumor immunity through an immune-based mechanism. Clin Cancer Res. Jul. 1, 2007;13(13):3951-9.

Mauro et al., 2001, Chronic Myelogenous Leukemia, Current Opinion Oncology 13:3-7.

McGirt et al., Independent association of extent of resection with survival in patients with malignant brain astrocytoma. J Neurosurg. Jan. 2009;110(1):156-62. doi: 10.3171/2008.4.17536.

McMurry, Organic Chemistry, 4th ed. Brooks/Cole Published Company, Pacific Grove, CA 1996, §§ 28.5 and 28.6, pp. 1108-1113.

Melcher et al., 1998, Tumor immunogenicity is determined by the mechanism of cell death via induction of heat shock protein expression, Nat. Med. 5:581-587.

Menoret et al., 1995, Co-segregation of tumor immunogenicity with expression of inducible but not constitutive hsp70 in rat colon carcinomas, J. Immunol. 155:740-747.

Mitsuda et al., 1993, A receptor-mediated antigen delivery and incorporation system: Administration of alpha 2-macroglobulin-cytochrome c conjugate induced high concentrations of antibodies against cytochrome c in mice, Biochem. Biophys. Res. Commun. 191(3):1326-1331.

Mizzen et al., 1998, Immune responses to stress proteins: applications to infectious disease and cancer, Biotherapy 10:173-185.

Molldrem et al., 1999, A PR1-Human Leukocyte Antigen-A2 Tetramer Can Be Used to Isolate Low-Frequency Cytotoxic T Lymphocytes from Healthy Donors That Selectively Lyse Chronic Myelogenous Leukemia, Cancer Research 59: 2675-2681.

Molldrem et al., 2000, Evidence that specific T lymphocytes may participate in the elimination of chronic myelogenous leukemia, Nature Medicine 6(9):1018-1023.

Munro et al., 1986, An Hsp70-like protein in the ER: identity with the 78 kd glucose-regulated protein and immunoglobulin heavy chain binding protein, Cell 46(2):291-300.

Narod, 1995, Screening for cancer in high risk families, Clin. Biochem. 28(4):367-372.

Nielsen et al., 1996, Identification of residues in alpha-macroglobulins important for binding to the alpha2-macroglobulin receptor/Low density lipoprotein receptor-related protein, J. Biol. Chem. 271(22):12909-12912.

Nishimura et al. The critical role of Th1-dominant immunity in tumor immunology, Cancer Chemother Pharmacol. 2000, vol. 46:S52-S61.

Ohashi et al., 2000, Cutting edge: heat shock protein 60 is a putative endogenous ligand of the toll-like receptor-4 complex, J. Immunol. 164:558-561.

Osada et al., 1987, Murine T cell proliferation can be specifically augmented by macrophages fed with specific antigen: alpha-2-macroglobulin conjugate, Biochem. Biophys. Res. Commun. 146(1):26-31.

Osada et al., 1988, Antibodies against viral proteins can be produced effectively in response to the increased uptake of alpha 2-macroglobulin:viral protein conjugate by macrophages, Biochem. Biophys. Res. Commun. 150(2):883-889.

Pal et al., 1992, Immunization with extracellular proteins of *Mycobacterium tuberculosis* induces cell-mediated immune responses and substantial protective immunity in a guinea pig model of pulmonary tuberculosis, Infect. Immun. 60(11):4781-4792.

Pardoll, 2000, Therapeutic vaccination for cancer, Clin. Immunol. 95(1 Pt 2): S44-62.

Parsa et al., Autologous heat shock protein vaccine (HSPPC-96) for patients with recurrent glioblastoma (GBM): Results of a phase II multicenter clinical trial with immunological assessments. 2011 ASCO Annual Meeting. J Clin Oncol 29: 2011. Abstract 2565.

Pazdur, FDA Approval for Bevacizumab. National cancer institute. Jan. 25, 2013. Last accessed at http://www.cancer.gov/cancertopics/druginfo/fda-bevacizumab/print on Jun. 10, 2013.

Peelen et al., 1996, The majority of 22 Dutch high-risk breast cancer families are due to either BRCA1 or BRCA2, Eur. J. Hum. Genet. 4(4):225-230.

Pinilla-Ibarz et al., 2000, Vaccination of patients with chronic myelogenous leukemia with bcr-abl oncogene breakpoint fusion peptides generates specific immune responses, Blood 95(5):1781-1787.

Plate et al., Vascular endothelial growth factor and glioma angiogenesis: coordinate induction of VEGF receptors, distribution of VEGF protein and possible in vivo regulatory mechanisms. Int J Cancer. Nov. 15, 1994;59(4):520-9.

Plate, Mechanisms of angiogenesis in the brain. J Neuropathol Exp Neurol. Apr. 1999;58(4):313-20.

Presta et al., Humanization of an anti-vascular endothelial growth factor monoclonal antibody for the therapy of solid tumors and other disorders. Cancer Res. Oct. 15, 1997;57(20):4593-9.

Rescigno et al., 1998, Dendritic cell survival and maturation are regulated by different signaling pathways, J. Exp. Med. 188:2175-2180.

Rini et al., Combination immunotherapy with prostatic acid phosphatase pulsed antigen-presenting cells (provenge) plus bevacizumab in patients with serologic progression of prostate cancer after definitive local therapy. Cancer. Jul. 1, 2006;107(1):67-74.

Riordan et al. Herimycin A accelerates the induction of apoptosis following etoposide treatment or gamma-irradiation of bcr/abl-positive leukemia cells, Oncogene, 1998, 16(12):1533-1542.

Rozendaal et al., 1996, PCR-based high-risk HPV test in cervical cancer screening gives objective risk assessment of women with cytomorphologically normal cervical smears, Int. J. Cancer 68(6):766-769.

Ruzevick, A phase I trial of a heat shock protein vaccine (HSPPC-96) in combination with Gliadel for treatment of recurrent glioblastoma multiforme (GBM). Jul. 22, 2011.

Sanai et al., An extent of resection threshold for newly diagnosed glioblastomas. J Neurosurg. Jul. 2011;115(1):3-8. doi: 10.3171/2011.2.JNS10998. Epub Mar. 18, 2011.

Sano et al., 1987, The augmentation of tumor-specific immunity using haptenic muramyl dipeptide (MDP) derivatives. II. Establishment of tumor-specific immunotherapy models utilizing MDP hapten-reactive helper T cell activity, Cancer Immunol. Immunother. 25(3):180-184.

Sato et al, Immunotherapy using heat-shock protein preparations of leukemia cells after syngeneic bone marrow transplantation in mice, Blood (2001) 98:1852-1857.

Sauter et al., 2000, Consequences of cell death: exposure to necrotic tumor cells, but not primary tissue cells or apoptotic cells, induces the maturation of immunostimulatory dendritic cells, J. Exp. Med. 191:423-434.

Shrimali et al., Antiangiogenic agents can increase lymphocyte infiltration into tumor and enhance the effectiveness of adoptive immunotherapy of cancer. Cancer Res. Aug. 1, 2010;70(15):6171-80. doi: 10.1158/0008-5472.CAN-10-0153. Epub Jul. 14, 2010.

Silva et al., 1994, A single mycobacterial protein (hsp 65) expressed by a transgenic antigen-presenting cell vaccinates mice against tuberculosis, Immunology 82(2):244-248.

Silver et al., 1999, An evidence-based analysis of the effect of busulfan, hydroxyurea, interferon, and allogeneic bone marrow transplantation in treating the chronic phase of chronic myeloid leukemia: developed for the American Society of Hematology, Blood 94(5):1517-1536.

Simizu et al., 1994, Induction of apoptosis by erbstatin in mouse leukemia L1210 cells, Bioscience, Biotechnology and Biochemistry 58(9):1549-1552.

Simons et al., Bioactivity of autologous irradiated renal cell carcinoma vaccines generated by ex vivo granulocyte-macrophage colony-stimulating factor gene transfer. Cancer Res. Apr. 15, 1997;57(8):1537-46.

Sorger et al., 1987, The glucose-regulated protein grp94 is related to heat shock protein hsp90, J. Mol. Biol. 194(2):341-344.

Spraycar, 1995, Stedman's Medical Dictionary, 26.sup.th edition, Williams & Wilkins, Baltimore, MD, pp. 1899, 1900.

Srivastava et al., 1988, Chromosomal assignment of the gene encoding the mouse tumor rejection antigen gp96, Immunogenetics 28(3):205-207.

Srivastava et al., 1991, Stress-induced proteins in immune response to cancer, Curr. Top. Microbiol. Immunol. 167:109-123.

(56) References Cited

OTHER PUBLICATIONS

Srivastava, 1993, Peptide-binding heat shock proteins in the endoplasmic reticulum: role in immune response to cancer and in antigen presentation, Adv. Cancer Res. 62:153-177.

Srivastava, 2002, Epub Oct. 4, 2001, Interaction of Heat Shock Proteins with peptides and antigen presenting cells: chaperoning of the innate and adaptive immune responses, Annu. Rev. Immunol. 20:395-425.

Stack et al., 1982, Autologous x-irradiated tumour cells and percutaneous BCG in operable lung cancer, Thorax 37(8):588-593.

Stevenson, 1999, DNA vaccines against cancer: from genes to therapy, Ann. Oncol. 10:1413-1418.

Stummer et al., Extent of resection and survival in glioblastoma multiforme: identification of and adjustment for bias. Neurosurgery. Mar. 2008;62(3):564-76; discussion 564-76. doi: 10.1227/01.neu.0000317304.31579.17.

Stupp et al., Radiotherapy plus concomitant and adjuvant temozolomide for glioblastoma. N Engl J Med. Mar. 10, 2005;352(10):987-96.

Stupp et al., Effects of radiotherapy with concomitant and adjuvant temozolomide versus radiotherapy alone on survival in glioblastoma in a randomised phase III study: 5-year analysis of the EORTC-NCIC trial. Lancet Oncol. May 2009;10(5):459-66. doi: 10.1016/S1470-2045(09)70025-7. Epub Mar. 9, 2009.

Sul, Peptide-based glioma vaccine IMA950 in patients with glioblastoma. Clinical trials. Immatics biotechnologies gmbh. Jul. 21, 2011.

Suto et al., 1995, A mechanism for the specific immunogenicity of heat shock protein-chaperoned peptides, Science 269:1585-1588.

Suzue et al., 1996, Adjuvant-free hsp70 fusion protein system elicits humoral and cellular immune responses to HIV-1 p24, J. Immunol. 156(2):873-879.

Suzue et al., 1996, Heat shock proteins as immunological carriers and vaccines, in: Stress-Inducible Cellular Responses, U. Feige, R. I. Morimoto, I. Yahara, B. S. Polla, eds., Birkhauser/Springer, 77:451-465.

Suzue et al., 1997, Heat shock fusion proteins as vehicles for antigen delivery into the major histocompatibility complex class I presentation pathway, Proc. Natl. Acad. Sci. USA 94(24):13146-13151.

Tamura et al., 1997, Immunotherapy of tumors with autologous tumor-derived heat shock protein preparations, Science 278(5335):117-120.

Tewari et al., Incorporation of bevacizumab in the treatment of recurrent and metastatic cervical cancer: A phase III randomized trial of the Gynecologic Oncology Group. J Clin Oncol. 2013;31. Abstract 03.

Thomas et al., 2002, Cytogenetic Profile of Chronic Myeloid Leukemias, Indian J. Cancer 39:61-65.

Todryk et al., 1999, Heat shock protein 70 induced during tumor cell killing induces Th1 cytokines and targets immature dendritic cell precursors to enhance antigen uptake, J. Immunol. 163:1398-1408.

Udono et al., 1993, Heat shock protein 70-associated peptides elicit specific cancer immunity, J. Exp. Med. 178:1391-1396.

Udono, et al., 1994, Comparison of tumor-specific immunogenecities of stress-induced proteins gp96, hsp90 and hsp70, J. Immunol. 152:5398-5403.

Van Bergen En Henegouwen et al., 1987, Induction of the heat shock regulon does not produce thermotolerance in *Escherichia coli*, Genes Dev. 1(6):525-531.

Van Oosterom et al., 2001 Safety and efficacy of imatinib (ST1571) in metastitic gastrointenstinal stromal tumors: a phase 1 study: The Lancet, Lancet Limited, London, GB vol. 358(9291):1421-1423.

Vargas-Roig et al., Heat shock protein expression and drug resistance in breast cancer patients treated with induction chemotherapy. Int J Cancer. Oct. 23, 1998;79(5):468-75.

Wang et al., 2001, Characterization of heat shock protein 110 and glucose-regulated protein 170 as cancer vaccines and the effect of fever-range hyperthermia on vaccine activity, J. Immunol. 166(1):490-497.

Wang et al., 2002, Serial monitoring of BCR-ABL by peripheral blood real time polymerase chain reaction predicts the marrow cytogenetic response to imatinib mesylate in chronic myeloid leukemia, British Journal of Haematology 118: 771-777.

Wefel et al., Neurocognitive function (NCF) outcomes in patients with glioblastoma (GBM) enrolled in RTOG 0825. J Clin Oncol. 2013;31. Abstract 2004.

Welch et al., 1985, Morphological study of the mammalian stress response: characterization of changes in cytoplasmic organelles, cytoskeleton, and nucleoli, and appearance of intranuclear actin filaments in rat fibroblasts after heat-shock treatment, J. Cell. Biol. 101:1198-1211.

Welch, 1993, How cells respond to stress, Sci. Am. 268(5):56-64.

Wick et al., Tumor response based on adapted Macdonald criteria and assessment of pseudoprogression (PsPD) in the phase III AVAglio trial of bevacizumab (Bv) plus temozolomide (T) plus radiotherapy (RT) in newly diagnosed glioblastoma (GBM). J Clin Oncol. 2013;31. Abstract 2002.

Wong et al., 1997, Dose-ranging study of indole-3-carbinol for breast cancer prevention, J. Cell. Biochem. Suppl. 28-29:111-116.

YaNagi et al., 1999, Simple and reliably sensitive diagnosis and monitoring of Philadelphia chromosome-positive cells in chronic myeloid leukemia by interphase fluorescence in situ hybridization of peripheral blood cells, Leukemia 13(4):542-552.

Yang et al., 1994, All-transretinoic acid reserves phorbol ester resistance in a human myeloid leukemia cell line, Blood vol. 83(2):490-496.

Yang et al., 1999, Murine dendritic cells transfected with human GP100 elicit both antigen-specific CD8+ and CD4+ T-cell responses and are more effective than DNA vaccines at generating anti-tumor immunity, Int. J. Cancer 83:532-540.

Young et al., 1990, Stress proteins and immunology, Ann. Rev. Immunol. 8:401-420.

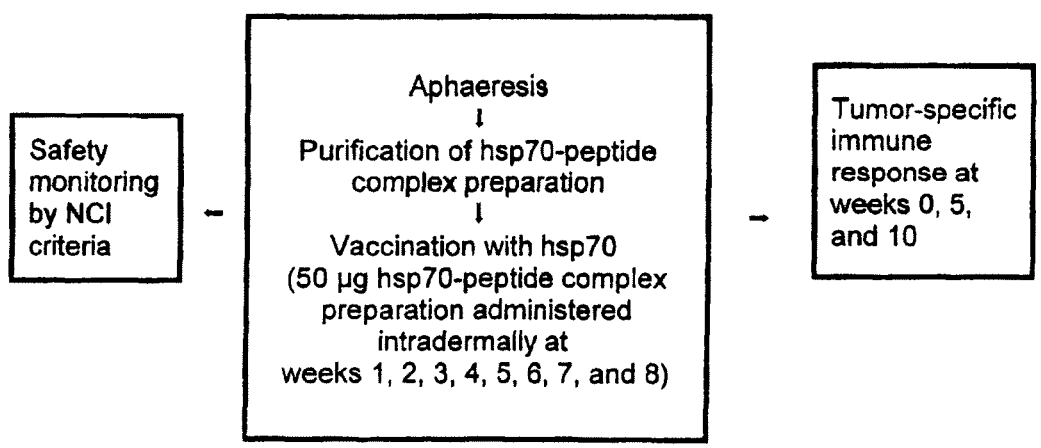

USING HEAT SHOCK PROTEINS TO IMPROVE THE THERAPEUTIC BENEFIT OF A NON-VACCINE TREATMENT MODALITY

RELATED APPLICATIONS

This application is a continuation application which claims the benefit under 35 U.S.C. §120 of U.S. application Ser. No. 13/250,141, entitled "USING HEAT SHOCK PROTEINS TO IMPROVE THE THERAPEUTIC BENEFIT OF A NON-VACCINE TREATMENT MODALITY" filed on Sep. 30, 2011, which is herein incorporated by reference in its entirety. Application Ser. No. 13/250,141 is a divisional application which claims the benefit under 35 U.S.C. §120 of U.S. application Ser. No. 12/418,724, entitled "USING HEAT SHOCK PROTEINS TO IMPROVE THE THERAPEUTIC BENEFIT OF A NON-VACCINE TREATMENT MODALITY" filed on Apr. 6, 2009, which is herein incorporated by reference in its entirety. Application Ser. No. 12/418,724 is a divisional application which claims the benefit under 35 U.S.C. §120 of U.S. application Ser. No. 11/283,103, entitled "USING HEAT SHOCK PROTEINS TO IMPROVE THE THERAPEUTIC BENEFIT OF A NON-VACCINE TREATMENT MODALITY" filed on Nov. 18, 2005, which is herein incorporated by reference in its entirety. Application Ser. No. 11/283,103 is a divisional application which claims the benefit under 35 U.S.C. §120 of U.S. application Ser. No. 10/322,312, entitled "USING HEAT SHOCK PROTEINS TO IMPROVE THE THERAPEUTIC BENEFIT OF A NON-VACCINE TREATMENT MODALITY" filed on Dec. 16, 2002, which is herein incorporated by reference in its entirety. Application Ser. No. 10/322,312 is a continuation-in-part application which claims the benefit under 35 U.S.C. §120 of U.S. application Ser. No. 10/131,961, entitled "USING HEAT SHOCK PROTEINS TO IMPROVE THE THERAPEUTIC BENEFIT OF A NON-VACCINE TREATMENT MODALITY" filed on Apr. 25, 2002, which is herein incorporated by reference in its entirety.

1. INTRODUCTION

The present invention relates to methods of improving a treatment outcome comprising administering a heat shock protein (HSP) preparation or an α-2-macroglobulin (α2M) preparation with a non-vaccine treatment modality. In particular, an HSP preparation or an α2M preparation is administered in conjunction with a non-vaccine treatment modality for the treatment of cancer or infectious diseases. In the practice of the invention, a preparation comprising HSPs such as but not limited to, hsp70, hsp90 and gp96 alone or in combination with each other, noncovalently or covalently bound to antigenic molecules or α2M, noncovalently or covalently bound to antigenic molecules is administered in conjunction with a non-vaccine treatment modality.

2. BACKGROUND OF THE INVENTION

Citation or discussion of a reference herein shall not be construed as an admission that such is prior art to the present invention.

2.1. Immune Responses

An organism's immune system reacts with two types of responses to pathogens or other harmful agents—humoral response and cell-mediated response (See Alberts, B. et al., 1994, Molecular Biology of the Cell. 1195-96). When resting B cells are activated by antigen to proliferate and mature into antibody-secreting cells, they produce and secrete antibodies with a unique antigen-binding site. This antibody-secreting reaction is known as the humoral response. On the other hand, the diverse responses of T cells are collectively called cell-mediated immune reactions. There are two main classes of T cells—cytotoxic T cells and helper T cells. Cytotoxic T cells directly kill cells that are infected with a virus or some other intracellular microorganism. Helper T cells, by contrast, help stimulate the responses of other cells: they help activate macrophages, dendritic cells and B cells, for example (See Alberts, B. et al., 1994, Molecular Biology of the Cell. 1228). Both cytotoxic T cells and helper T cells recognize antigen in the form of peptide fragments that are generated by the degradation of foreign protein antigens inside the target cell, and both, therefore, depend on major histocompatibility complex (MHC) molecules, which bind these peptide fragments, carry them to the cell surface, and present them there to the T cells (See Alberts, B. et al., 1994, Molecular Biology of the Cell. 1228). MHC molecules are typically found in abundance on antigen-presenting cells (APCs).

2.2. Chronic Myeloid Leukemia

Chronic myeloid (myelogenous, myelocytic, granulocytic) leukemia ("CML") is a cancer of the blood and bone marrow characterized by overproduction of white blood cells. CML is characterized by a chronic phase with a median duration of 3 to 5 years when treated with conventional agents and an accelerated or acute phase of approximately 3 to 6 months duration, inevitably terminating fatally. Initially, the chronic phase is characterized by no or few symptoms and signs. However, in the majority of cases, constitutional symptoms and abnormal physical findings including extramedullary abnormalities, such as myeloblastomas, eventually develop.

CML accounts for 7% to 20% of all leukemias and affects an estimated 1 to 2/100,000 persons in the general population. The American Cancer Society estimates that there will be about 4,400 new cases of CML in the United States this year.

CML is caused by a specific cytogenetic abnormality, the Philadelphia ("Ph+") chromosome, which results in a clonal myeloproliferative disorder of pluripotent hematopoietic stem cells (Faderl et al., 1999, New England J. Med. 341(3): 164-172). The Ph+ chromosome results from a balanced translocation between the long arms of chromosomes 9 and 22, resulting in the bcr/abl chimeric gene that expresses an abnormal fusion protein with altered tyrosine kinase activity.

Current treatment options for patients in the chronic phase of CML include busulfan (BUS), hydroxyurea (HU), interferon (IFN)-based regimens, specific kinase inhibitor for bcr/abl or bone marrow/stem cell transplantation (BMT) (Silver et al., 1999, Blood 94(5):1517-1536). Until a few years ago, allogeneic BMT was the treatment of choice for all eligible patients, because it was the only treatment that appeared to change the natural course of the disease. Studies showed that at least half of the patients transplanted remain alive 5 to 10 years after the treatment. However, this practice was still complicated by the lack of donors, and the significant transplant related complications such as graft versus host diseases and infections. IFN-based regimens have also influenced the natural course of CML. However, IFN-based regiments alone only offer survival advantage by a median of about 20 months (Chronic Myeloid Leukemia Trialists' Collaborative Group, 1997, J. Natl. Cancer Inst. 89(21):1616-20).

Specific bcr/abl inhibitors such as Gleevec™ (imatinib mesylate, Novartis™) have shown promise in the phase I clinical trials. Drucker and Lydon, 2000, J. Clin. Invest. 105 (1):3-7; Dazzi et al., 2000, Leukemia 14:419-426; see also Hellman, Principles of Cancer Management: 6th edition, 2001, DeVita et al., eds., J.B. Lippencott Company, Philadelphia, which is hereby incorporated by reference in its entirety, pp. 2443-2444. Gleevec™ (imatinib mesylate) is also known as signal transduction inhibitor 571, STI-571, and CGP 57148. Based on the phase II studies (Druker et al., 2001, New England J. Med. 344(14):1031-1037, and Druker et al., 2001, New England J. Med. 344(14):1038-1042) the FDA has approved the use of Gleevec™ to treat the following three phases of CML: chronic phase that is no longer responding to the standard therapy, interferon; accelerated phase; and myeloid blast crisis. The long-term efficacy and toxicity, however, remain unknown. Furthermore, adverse effects have been observed in Gleevec™-treated patients including edema, hepatotoxicity, and hematologic toxicity. *Physician's Desk Reference* (56$^{th}$ ed., 2002). In addition, resistance to Gleevec™ has already been described. Le Coutre et al., 2000, Blood 95(5): 1758-1766. Thus, there is a need in the art for improved methods of treating CML.

2.3. Heat Shock Proteins

Heat shock proteins (HSPs), which are also referred to interchangeably herein as stress proteins, can be selected from among any cellular protein that satisfies the following criteria. It is a protein whose intracellular concentration increases when a cell is exposed to a stressful stimuli, it is capable of binding other proteins or peptides, it is capable of releasing the bound proteins or peptides in the presence of adenosine triphosphate (ATP) or low pH, and it is a protein showing at least 35% homology with any cellular protein having any of the above properties. HSPs include constitutively expressed conserved cellular homologs of the proteins induced by stress. Therefore it is contemplated that stress proteins/HSPs include other proteins, muteins, analogs, and variants thereof having at least 35% to 55%, preferably 55% to 75%, and most preferably 75% to 85% amino acid identity with members of the three families with the above properties.

The first stress proteins to be identified were the HSPs. As their name implies, HSPs are synthesized by a cell in response to heat shock. To date, three major families of HSPs have been identified based on molecular weight. The families have been called hsp60, hsp70 and hsp90 where the numbers reflect the approximate molecular weight of the stress proteins in kilodaltons. Many members of these families were found subsequently to be induced in response to other stressful stimuli including, but not limited to, nutrient deprivation, metabolic disruption, oxygen radicals, and infection with intracellular pathogens. (See Welch, May 1993, *Scientific American* 56-64; Young, 1990, *Annu. Rev. Immunol.* 8:401-420; Craig, 1993, *Science* 260:1902-1903; Gething, et al., 1992, *Nature* 355:33-45; and Lindquist, et al., 1988, *Annu. Rev. Genetics* 22:631-677), the disclosures of which are incorporated herein by reference. It is contemplated that hsps/stress proteins belonging to all of these three families can be used in the practice of the instant invention.

HSPs are intracellular molecules that are abundant, soluble, and highly conserved. As intracellular chaperones, HSPs participate in many biochemical pathways of protein maturation and function active during times of stress and normal cellular homeostasis. Many stresses can disrupt the three-dimensional structure, or folding, of a cell's proteins. Left uncorrected, mis-folded proteins form aggregates that may eventually kill the cell. HSPs bind to those damaged proteins, helping them refold into their proper conformations.

In normal (unstressed) cellular homeostasis, HSPs are required for cellular metabolism. HSPs help newly synthesized polypeptides fold and thus prevent premature interactions with other proteins. Also, HSPs aid in the transport of proteins throughout the cell's various compartments.

The major HSPs can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch et al., 1985, J. Cell. Biol. 101:1198-1211). In contrast, hsp90 and hsp60 proteins are abundant at normal temperatures in most, but not all, mammalian cells and are further induced by heat (Lai et al., 1984, Mol. Cell. Biol. 4:2802-2810; van Bergen en Henegouwen et al., 1987, Genes Dev. 1:525-531).

HSPs have been found to have immunological and antigenic properties. Immunization of mice with gp96 or p84/86 isolated from a particular tumor rendered the mice immune to that particular tumor, but not to antigenically distinct tumors (Srivastava, P. K. et al., 1988, Immunogenetics 28:205-207; Srivastava, P. K. et al., 1991, Curr. Top. Microbiol. Immunol. 167:109-123). Further, hsp70 was shown to elicit immunity to the tumor from which it was isolated but not to antigenically distinct tumors. However, hsp70 depleted of peptides was found to lose its specific immunogenic activity (Udono, M., and Srivastava, P. K., 1993, J. Exp. Med. 178:1391-1396). These observations suggested that the heat shock proteins are not antigenic per se, but form noncovalent complexes with antigenic peptides, and the complexes can elicit specific immunity to the antigenic peptides (Srivastava, P. K., 1993, Adv. Cancer Res. 62:153-177; Udono, H. et al., 1994, J. Immunol., 152:5398-5403; Suto, R. et al., 1995, Science, 269:1585-1588). Recently, hsp60 and hsp70 have been found to stimulate production of proinflammatory cytokines, such as TNFα and IL-6, by monocytes, macrophages, or cytotoxic T cells (Breloer et al., 1999, J. Immunol. 162:3141-3147; Chen et al., 1999, J. Immunol. 162:3212-3219; Ohashi et al., 2000, J. Immunol. 164:558-561; Asea et al., 2000, Nature Medicine, 6:435-442; Todryk et al, 1999, J. Immunol. 163:1398-1408). Hsp70 has also been shown to target immature dendritic cells and make them more able to capture antigens (Todryk et al., J. Immunol. 163:1398-1408). It has been postulated that release of or induction of expression of hsp60 and hsp70, e.g., due to cell death, may serve to signal that an immune reaction should be raised (Chen et al., 1999, J. Immunol. 162:3212-3219; Ohashi et al., 2000, J. Immunol. 164: 558-561; Todryk et al., 1999, J. Immunol. 163:1398-1408).

The use of noncovalent complexes of HSP and peptide, purified from cancer cells, for the treatment and prevention of cancer has been described in U.S. Pat. Nos. 5,750,119, 5,837, 251, and 6,017,540.

The use of HSP-peptide complexes for sensitizing antigen presenting cells in vitro for use in adoptive immunotherapy is described in U.S. Pat. Nos. 5,985,270 and 5,830,464.

HSP-peptide complexes can also be isolated from pathogen-infected cells and used for the treatment and prevention of infection caused by the pathogen, such as viruses, and other intracellular pathogens, including bacteria, protozoa, fungi and parasites; see U.S. Pat. Nos. 5,961,979, and 6,048,530.

Immunogenic HSP-peptide complexes can also be prepared by in vitro complexing of HSPs and antigenic peptides, and the uses of such complexes for the treatment and prevention of cancer and infectious diseases has been described in U.S. Pat. Nos. 5,935,576, and 6,030,618. The use of heat shock protein in combination with a defined antigen for the treatment of cancer and infectious diseases have also been described in PCT publication WO97/06821 dated Feb. 27, 1997.

The purification of HSP-peptide complexes from cell lysate has been described previously; see for example, U.S. Pat. Nos. 5,750,119, and 5,997,873.

2.4. α2-Macroglobulin

The α-macroglobulins are members of a protein superfamily of structurally related proteins which also comprises complement components C3, C4 and C5. The human plasma protein alpha(2)macroglobulin (α2M) is a 720 kDa homotetrameric protein primarily known as proteinase inhibitor and plasma and inflammatory fluid proteinase scavenger molecule (for review see Chu and Pizzo, 1994, Lab. Invest. 71:792). Alpha (2) macroglobulin is synthesized as a 1474 amino acid precursor, the first 23 of which function as a signal sequence that is cleaved to yield a 1451 amino acid mature protein (Kan et al., 1985, Proc. Natl. Acad. Sci. U.S.A. 82:2282-2286).

Alpha(2)macroglobulin promiscuously binds to proteins and peptides with nucleophilic amino acid side chains in a covalent manner (Chu et al., 1994, Ann. N.Y. Acad. Sci. 737:291-307) and targets them to cells which express the α2M receptor (α2MR) (Chu and Pizzo, 1993, J. Immunol. 150:48). Binding of α2M to the α2MR is mediated by the C-terminal portion of α2M (Holtet et al., 1994, FEBS Lett. 344:242-246) and key residues have been identified (Nielsen et al., 1996, J. Biol. Chem. 271:12909-12912).

Generally known for inhibiting protease activity, α2M binds to a variety of proteases thorough multiple binding sites (see, e.g., Hall et al., 1981, Biochem. Biophys. Res. Commun. 100(1):8-16). Protease interaction with α2M results in a complex structural rearrangement called transformation, which is the result of a cleavage within the "bait" region of α2M after the proteinase becomes "trapped" by thioesters. The conformational change exposes residues required for receptor binding, allowing the α2M-proteinase complex to bind to the α2MR. Methylamine can induce similar conformational changes and cleavage as that induced by proteinases. The uncleaved form of α2M, which is not recognized by the receptor, is often referred to as the "slow" form (s-α2M). The cleaved form is referred to as the "fast" form (f-α2M) (reviewed by Chu et al., 1994, Ann. N.Y. Acad. Sci. 737:291-307).

Studies have shown that, in addition to its proteinase-inhibitory functions, α2M, when complexed to antigens, can enhance the antigens' ability to be taken up by antigen presenting cells such as macrophages and presented to T cell hybridomas in vitro by up to two orders of magnitude (Chu and Pizzo, 1994, Lab. Invest. 71:792), and induce T cell proliferation (Osada et al., 1987, Biochem. Biophys. Res. Commun. 146:26-31). Further evidence suggests that complexing antigen with α2M enhances antibody production by crude spleen cells in vitro (Osada et al., 1988, Biochem. Biophys. Res. Commun. 150:883) and elicits an in vivo antibody responses in experimental rabbits (Chu et al., 1994, J. Immunol. 152:1538-1545) and mice (Mitsuda et al., 1993, Biochem. Biophys. Res. Commun. 101:1326-1331). However, none of these studies have shown whether α2M-antigen complexes are capable of eliciting cytotoxic T cell responses in vivo.

α2M can form complexes with antigens, which are taken up by antigen presenting cells ("APCs") via the α2MR, also known as LDL (low-density lipoprotein) Receptor-Related Protein ("LRP") or CD91 (see PCT/US01/18047, which is incorporated by reference herein in its entirety). α2M directly competes for the binding of heat shock protein gp96 to the α2MR, indicating that α2M and hsps may bind to a common recognition site on the α2MR (Binder et al., 2000, Nature Immunology 1(2), 151-154). Additionally, α2M-antigenic peptide complexes prepared in vitro can be administered to animals to generate a cytotoxic T cell response specific to the antigenic molecules (Binder et al., 2001, J. Immunol. 166: 4968-72). Thus, because hsps and α2M have a number of common functional attributes, such as the ability to bind peptide, the recognition and uptake by the α2MR, and the stimulation of a cytotoxic T cell response, α2M can be used for immunotherapy against cancer and infectious diseases.

3. SUMMARY OF INVENTION

The present invention is based, in part, on the recognition that an HSP preparation can enhance or improve the therapeutic benefit of non-vaccine treatment modalities or therapeutic modalities for treatment of cancer or infectious diseases. Thus, the present invention encompasses methods and compositions that comprise administering an HSP preparation in combination with a non-vaccine treatment modality. Also encompassed are methods and compositions that comprise administering an α2M preparation in combination with a non-vaccine treatment modality. In particular, the invention encompasses methods and compositions of treatment and compositions that provide a better therapeutic profile than that of an HSP preparation or α2M preparation administered alone or a non-vaccine treatment modality administered alone. The source of the HSP or α2M is preferably an eukaryote, and most preferably a mammal. The subject receiving the treatment is preferably a mammal including, but not limited to, domestic animals, such as cats and dogs; wild animals, including foxes and raccoons; livestock and fowl, including horses, cattle, sheep, turkeys and chickens, as well as any rodents. Most preferably, the subject is human.

The invention provides methods for improving the therapeutic outcome of a non-vaccine treatment modality comprising administering either an HSP preparation or an α2M preparation, preferably a purified HSP preparation or a purified α2M preparation, in conjunction with the administration of the treatment modality. Either the HSP preparation or the α2M preparation can be administered over a period of time which may precede, overlap, and/or follow a treatment regimen with a non-vaccine treatment modality. The HSP preparation or the α2M preparation can be administered concurrently, before, or after the administration of the treatment modality. Examples of treatment modalities include but are not limited to antibiotics, antivirals, antifungal compounds, anti-cancer treatments such as chemotherapeutic agents, and radiation, as well as biological therapeutic agents and immunotherapeutic agents. In preferred embodiments, the treatment modality is useful in the treatment or prevention of cancer. In particularly preferred embodiments, the treatment modality is useful in the treatment or prevention of chronic myelgenous leukemia or soft tissue sarcomas including but not limited to gastrointestinal stromal tumors. In another preferred embodiment, the treatment modality is Gleevec™.

In one embodiment, the invention encompasses methods of treatment that provide better therapeutic profiles than the administration of the treatment modality or the HSP preparation alone. In another embodiment, the invention encompasses methods of treatment that provide better therapeutic profiles than the administration of the treatment modality or the α2M preparation alone. Encompassed by the invention are methods wherein the administration of a treatment modality with an HSP preparation or an α2M preparation has additive potency or additive therapeutic effect. The invention also encompasses synergistic outcomes where the therapeutic efficacy is greater than additive. Preferably, such administration of a treatment modality with an HSP preparation or with an α2M preparation also reduces or avoids unwanted or adverse effects. Given the invention, in certain embodiments, doses of non-vaccine treatment modality can be reduced or administered less frequently, preferably increasing patient compliance, improving therapy and/or reducing unwanted or adverse effects. In a specific embodiment, lower or less frequent doses of chemotherapy or radiation therapy are administered to reduce or avoid unwanted effects. Alternatively, doses of HSP preparation and doses of α2M preparation can be reduced or administered less frequently if administered with a treatment modality.

In one embodiment, the present invention provides a method for improving the outcome of a treatment in a subject receiving a therapeutic modality which is not a vaccine. The method comprises administering either a heat shock protein preparation, preferably a purified HSP preparation, or an α2M preparation, preferably a purified α2M preparation, to the subject before, concurrently with, or after the administration of the therapeutic modality. In a specific embodiment, the HSP preparation or the α2M preparation can augment the therapeutic benefit of a treatment modality and improve the outcome of the treatment. Without being bound by any theory or mechanism, the administration of a mammalian HSP preparation or α2M preparation to a subject can enhance the responsiveness of non-specific immune mechanisms of the subject, for example, by increasing the number of natural killer (NK) cells and/or accelerating the maturation of dendritic cells and/or can also enhance the responsiveness of specific immune mechanisms, such as by increasing the number of CD4+ and CD8+ T cells. In a preferred specific embodiment, the HSP preparation is administered before the administration of the therapeutic modality. In another preferred specific embodiment, the α2M preparation is administered before the administration of the therapeutic modality.

In another embodiment, the present invention provides a method for improving the outcome of a treatment in a subject receiving an HSP preparation, preferably a purified HSP preparation, by administering a non-vaccine therapeutic modality to the subject before, concurrently with, or after the administration of the HSP preparation. In a specific embodiment, the non-vaccine therapeutic modality can augment the therapeutic benefit of an HSP preparation and improve the outcome of the treatment.

In another embodiment, the present invention provides a method for improving the outcome of a treatment in a subject receiving an α2M preparation, preferably a purified α2M preparation, by administering a non-vaccine therapeutic modality to the subject before, concurrently with, or after the administration of the α2M preparation. In a specific embodiment, the non-vaccine therapeutic modality can augment the therapeutic benefit of an α2M preparation and improve the outcome of the treatment.

In certain embodiments, the administration of the HSP/α2M preparation in the absence of administration of the therapeutic modality or the administration of the therapeutic modality in the absence of administration of the HSP/α2M preparation is not therapeutically effective. In a specific embodiment, the amount of HSP/α2M preparation or therapeutic modality is administered in an amount insufficient to be therapeutically effective alone. In alternate embodiments, both or at least one of the HSP/α2M preparation or therapeutic modality is therapeutically effective when administered alone.

In various embodiments, the methods comprise the administration of an HSP preparation, preferably a purified HSP preparation, to a subject receiving a treatment modality for the treatment of cancer or infectious diseases. Preferably the HSP preparation comprises HSP-peptide complexes displaying the antigenicity of a tumor specific antigen or tumor associated antigen of the type of cancer or an antigen of an infectious agent, i.e., heat shock proteins complexed to antigenic peptides of the cancer cells or infected cells from which the complexes are obtained. Accordingly, in one embodiment, the specific immunogenicity of the HSP preparation derives from the peptide complexed to the HSP. In preferred embodiments, the HSP-peptide complexes are isolated from an antigen source such as cancer tissues, cancer cells, or infected tissues. In the practice of the invention, such HSP-peptide complexes are preferably, autologous to the individual subject, i.e., obtained from the tissues of the subject receiving the administration of HSP preparation and treatment modality, but need not be (i.e., allogeneic to the individual subject).

In various other embodiments, the methods comprise the administration of an α2M preparation, preferably a purified α2M preparation, to a subject receiving a treatment modality for the treatment of cancer or infectious diseases. Preferably the α2M preparation comprises α2M-peptide complexes displaying the antigenicity of a tumor specific antigen or tumor associated antigen of the type of cancer or an antigen of an infectious agent, i.e., α2M complexed to antigenic peptides of the cancer cells or infected cells from which the complexes are obtained. Accordingly, in one embodiment, the specific immunogenicity of the α2M preparation derives from the peptide complexed to the α2M. In preferred embodiments, the α2M-peptide complexes are isolated from an antigen source such as cancer tissues, cancer cells, or infected tissues. In the practice of the invention, such α2M-peptide complexes are preferably, autologous to the individual subject, i.e., obtained from the tissues of the subject receiving the administration of α2M preparation and treatment modality, but need not be (i.e., allogeneic to the individual subject).

In one embodiment, the methods comprise the administration of an HSP preparation or an α2M preparation, preferably a purified HSP preparation or a purified α2M preparation, to a subject receiving a treatment modality for treatment of an infectious disease. Such treatment modalities are known in the art and include but are not limited to antibiotics, antivirals, antifungals as well as biological and immunotherapeutic agents. Preferably the HSP preparation comprises HSP-peptide complexes which display the antigenicity of an agent of the infectious disease. Preferably the α2M preparation comprises α2M-peptide complexes which display the antigenicity of an agent of the infectious disease. In a specific embodiment, the outcome of a treatment of a type of infectious disease in a subject receiving a non-vaccine therapeutic modality is improved by administering HSP-peptide complexes comprising an HSP complexed to a peptide that displays the antigenicity of an antigen of an agent of said type of infectious disease. Preferably, the HSP-peptide complexes are not present in admixture with HSP or α2M that is not complexed to a peptide that displays the antigenicity of an antigen of an agent of the same infectious disease. (See International Application No. PCT/US01/28840, filed Sep. 15, 2001, incorporated by reference herein in its entirety). In one embodiment, the HSP preparation is administered prior to administration of the therapeutic modality. In another embodiment, the therapeutic modality is administered prior to the administration of the HSP preparation. In another specific embodiment, the outcome of a treatment of a type of infectious disease in a subject receiving a non-vaccine therapeutic modality is improved by administering α2M-peptide complexes comprising an α2M complexed to a peptide that displays the antigenicity of an antigen of an agent of said type of infectious disease. Preferably, the α2M-peptide complexes are not present in admixture with HSP or α2M that is not complexed to a peptide that displays the antigenicity of an antigen of an agent of the same infectious disease. In one embodiment, the α2M preparation is administered prior to administration of the therapeutic modality. In another embodiment the therapeutic modality is administered prior to the administration of the α2M preparation.

In another embodiment, the methods comprise the administration of either an HSP preparation or an α2M preparation, preferably a purified HSP preparation or a purified α2M preparation, to a subject receiving a treatment modality for treatment of cancer. Such treatment modalities include but are not limited to chemotherapies and radiation therapies as well as hormonal therapies, biological therapies and immunotherapies. Preferably the HSP preparation or α2M preparation is administered to a subject receiving chemotherapy or radiation therapy for treatment of cancer. Preferably the HSP preparation comprises HSP-peptide complexes which display the antigenicity of the type of cancer being treated.

Preferably where the preparation is an α2M preparation, the α2M preparation comprises α2M-peptide complexes which display the antigenicity of the type of cancer being treated. Accordingly, in preferred embodiments, the invention provides methods for improving the outcome of cancer treatment in a subject receiving a therapeutic modality which is not a vaccine using HSP-peptide complexes comprising an HSP complexed to a peptide that displays the antigenicity of a tumor specific antigen or tumor associated antigen of a type of cancer or using α2M-peptide complexes comprising an α2M complexed to a peptide that displays the antigenicity of a tumor specific antigen or tumor associated antigen of a type of cancer. In certain preferred embodiments, such HSP-peptide complexes and α2M-peptide complexes are not diluted with either HSP or α2M that is not complexed to a peptide that displays the antigenicity of an antigen of the same type of cancer. In one embodiment, the HSP preparation or α2M preparation is administered prior to administration of the therapeutic modality. In another embodiment, the therapeutic modality is administered prior to administration of the HSP preparation or α2M preparation.

In various embodiments, the HSP preparation or α2M preparation is administered with an anti-cancer agent which can be but is not limited to a cytotoxic agent, antimitotic agent, tubulin stabilizing agent, microtubule formation inhibiting agent, topoisomerase inhibitors, alkylating agent, DNA interactive agent, antimetabolite, RNA/DNA antimetabolite, DNA antimetabolite. In a specific embodiment, the anti-cancer agent is a chemotherapeutic.

In a specific embodiment, an HSP preparation is administered to a subject receiving a chemotherapeutic agent for treatment of cancer. In another preferred embodiment, an α2M preparation is administered to a subject receiving a chemotherapeutic agent for treatment of cancer. Such chemotherapeutic agents are known in the art and include but are not limited to: methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, doxorubicin, epirubicin, 5-fluorouracil, taxanes such as docetaxel and paclitaxel, leucovorin, levamisole, irinotecan, estramustine, etoposide, nitrosoureas such as carmustine and lomustine, vinca alkaloids, platinum compounds, mitomycin, gemcitabine, hexamethylmelamine, topotecan, tyrosine kinase inhibitors, tyrphostins, STI-571 or Gleevec™ (imatinib mesylate), herbimycin A, genistein, erbstatin, and lavendustin A.

In preferred embodiments, each of the methods above comprise administering either an HSP preparation or an α2M preparation, preferably a purified HSP preparation or a purified α2M preparation, to a subject receiving a drug of the 2-phenylaminopyrimidine class for treatment of cancer. More preferably, the subject is receiving Gleevec™ (i.e., imatinib mesylate) for treatment of cancer.

In another specific embodiment, an HSP preparation or an α2M preparation is administered to a subject receiving radiation therapy for treatment of cancer. For radiation treatment, the radiation can be gamma rays or X-rays. The methods encompass treatment of cancer comprising radiation therapy, such as external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J.B. Lippencott Company, Philadelphia. In preferred embodiments, the radiation treatment is administered as external beam radiation or teletherapy wherein the radiation is directed from a remote source. In various preferred embodiments, the radiation treatment is administered as internal therapy or brachytherapy wherein a radioactive source is placed inside the body close to cancer cells or a tumor mass.

In another embodiment, each of the above methods comprise the administration of HSP preparation, preferably a purified HSP preparation, to a subject receiving a combination of treatment modalities for the treatment of cancer. In another embodiment, each of the above methods comprise the administration of an α2M preparation, preferably a purified α2M preparation, to a subject receiving a combination of treatment modalities for the treatment of cancer. Preferably the HSP preparation and α2M preparation each comprises HSP-peptide complexes and α2M-peptide complexes, respectively, which display the antigenicity of the type of cancer being treated. In one such embodiment, an HSP preparation is administered to a subject receiving chemotherapy in combination with a biological therapy, preferably a cytokine. In another such embodiment, an α2M preparation is administered to a subject receiving chemotherapy in combination with a biological therapy, preferably a cytokine. In various embodiments, the cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, TGF-β, IL-15, IL-18, GM-CSF, INF-γ, INF-α, SLC, endothelial monocyte activating protein-2 (EMAP2), MIP-3α, MIP-3β, or an MHC gene, such as HLA-B7. Additionally, other exemplary cytokines include other members of the TNF family, including but not limited to TNF-α-related apoptosis-inducing ligand (TRAIL), TNF-α-related activation-induced cytokine (TRANCE), TNF-α-related weak inducer of apoptosis (TWEAK), CD40 ligand (CD40L), LT-α, LT-β, OX40L, CD40L, FasL, CD27L, CD30L, 4-1BBL, APRIL, LIGHT, TL1, TNFSF16, TNFSF17, and AITR-L, or a functional portion thereof. See, e.g., Kwon et al., 1999, Curr. Opin. Immunol. 11:340-345 for a general review of the TNF family. In one embodiment, the HSP preparation is administered prior to the treatment modalities. In another embodiment, the treatment modality is administered prior to the HSP preparation.

In a preferred embodiment, a purified HSP preparation is administered to a subject receiving cyclophosphamide in combination with IL-12 for treatment of cancer. In another preferred embodiment, a purified α2M preparation is administered to a subject receiving cyclophosphamide in combination with IL-12 for treatment of cancer.

In another embodiment, the above methods are useful for the prevention of cancer or infectious diseases. In a specific embodiment, an HSP preparation is administered in conjunction with a non-vaccine treatment modality to a subject to reduce the risk of acquiring a type of cancer or an infectious disease. In other specific embodiments, the methods encompass administration of an HSP preparation with administration of a non-vaccine treatment modality as a preventative measure to a subject having a genetic or non-genetic predisposition to a cancer or infectious disease or to a subject facing exposure to an agent of an infectious disease. In further embodiments, the invention also provides that each of the foregoing embodiments also can be applicable wherein an α2M preparation is administered in conjunction with a non-vaccine treatment modality.

The methods and compositions of the invention are useful not only in untreated patients, but are also useful in the treatment of patients partially or completely unresponsive to the therapeutic modality in the absence of the HSP/α2M preparation or to the HSP/α2M preparation in the absence of the therapeutic modality. In various embodiments, the invention provides methods and compositions useful in the treatment or prevention of diseases and disorders in patients that have been shown to be or may be refractory or non-responsive to therapies comprising the administration of either or both the HSP/α2M preparation or the therapeutic modality. The invention also includes methods and compositions comprising administration of the HSP/α2M preparation and the therapeutic modality to patients that have previously received and/or are concurrently receiving other forms of medical therapy.

The HSP preparation used in the methods and compositions of the invention is preferably purified, and can include free HSP not bound to any molecule, and molecular complexes of HSP with another molecule, such as a peptide. An HSP-peptide complex comprises an HSP covalently or non-covalently attached to a peptide. The methods of the invention may or may not require covalent or noncovalent attachment of an HSP to any specific antigens or antigenic peptides prior to administration to a subject. Although, the peptide(s) may be unrelated to the infectious disease or disorder or particular cancer being treated, in preferred embodiments, the HSP preparation comprises complexes which display the antigenicity of an antigen of the agent of infectious disease or of a tumor specific antigen or tumor associated antigen of the type of cancer being treated, respectively. More preferably, for the treatment of infectious disease, the HSP preparation comprises noncovalent HSP-peptide complexes isolated from a cell infected with an infectious agent (or non-infectious variant thereof displaying the antigenicity thereof) that causes the infectious disease. More preferably, for treatment of a type of cancer, the HSP preparation comprises noncovalent HSP-peptide complexes isolated from cancerous tissue of said type of cancer or a metastasis thereof, which can be from the patient (autologous) or not (allogeneic). Accordingly, for the purposes of this invention, an HSP preparation is a composition comprising HSPs whether unbound or bound to other molecules (e.g., peptides). The HSP is preferably purified. An HSP preparation may include crude cell lysate comprising HSP, the amount of lysate corresponding to between 100 to $10^8$ cell equivalents. HSPs can be conveniently purified from most cellular sources as a population of complexes of different peptides non-covalently bound to HSPs. The HSPs can be separated from the non-covalently bound peptides by exposure to low pH and/or adenosine triphosphate, or other methods known in the art.

The α2M preparation used in the methods and compositions of the invention is preferably purified, and can include free α2M not bound to any molecule, and molecular complexes of α2M with another molecule, such as a peptide. An α2M-peptide complex comprises an α2M covalently or non-covalently attached to a peptide. The methods of the invention may or may not require covalent or noncovalent attachment of an α2M to any specific antigens or antigenic peptides prior to administration to a subject. Although, the peptide(s) may be unrelated to the infectious disease or disorder or particular cancer being treated, in preferred embodiments, the α2M preparation comprises complexes which display the antigenicity of an antigen of the agent of infectious disease or of a tumor specific antigen or tumor associated antigen of the type of cancer being treated, respectively. More preferably, for the treatment of infectious disease, the α2M preparation comprises noncovalent α2M-peptide complexes isolated from a cell infected with an infectious agent (or non-infectious variant thereof displaying the antigenicity thereof) that causes the infectious disease. More preferably, for treatment of a type of cancer, the α2M preparation comprises noncovalent α2M-peptide complexes isolated from cancerous tissue of said type of cancer or a metastasis thereof, which can be from the patient (autologous) or not (allogeneic). Accordingly, for the purposes of this invention, an α2M preparation is a composition comprising α2M whether unbound or bound to other molecules (e.g., peptides). The α2M is preferably purified. An α2M preparation may include crude cell lysate comprising α2M, the amount of lysate corresponding to between 100 to $10^8$ cell equivalents. α2M s can be conveniently purified from most cellular sources as a population of complexes of different peptides non-covalently bound to α2Ms. The α2M can be separated from the non-covalently bound peptides by exposure to low pH and/or adenosine triphosphate, or other methods known in the art.

In various embodiments, the source of the HSP and the α2M is preferably an eukaryote, more preferably a mammal, and most preferably a human. Accordingly, the HSP preparation used by the methods of the invention includes eukaryotic HSPs, mammalian HSPs and human HSPs. The α2M preparation includes eukaryotic α2M, mammalian α2M and human α2M. The eukaryotic source from which the HSP preparation or α2M preparation is derived and the subject receiving the HSP preparation or the α2M preparation, respectively, are preferably the same species.

In one embodiment, the specific immunogenicity of the HSP preparation derives from the peptide complexed to a heat shock protein. Accordingly, in various embodiments, the HSP preparation comprises heat shock protein peptide complexes wherein the heat shock proteins are complexed to peptides derived from a specific antigen source. In a preferred embodiment, the HSP protein preparation comprises heat shock protein-peptide complexes that are autologous. In another preferred embodiment, the HSP preparation comprises heat shock proteins complexed to antigenic peptides of the cancer cells from which they are derived. In specific embodiments, the antigen is a tumor specific antigen (i.e., only expressed in the tumor cells). In other specific embodiments, the antigen is a tumor associated antigen (i.e., relatively overexpressed in the tumor cells). In yet another preferred embodiment, the HSP preparation comprises heat shock proteins complexed to antigenic peptides of the infected cells from which they are derived.

In another embodiment, the specific immunogenicity of the α2M preparation derives from the peptide complexed to an α2M. Accordingly, in various embodiments, the α2M preparation comprises α2M peptide complexes wherein the α2M are complexed to peptides derived from a specific antigen source. In a preferred embodiment, the α2M protein preparation comprises α2M-peptide complexes that are autologous. In another preferred embodiment, the α2M preparation comprises α2M complexed to antigenic peptides of the cancer cells from which they are derived. In other specific embodiments, the antigen is a tumor associated antigen (i.e., relatively overexpressed in the tumor cells). In yet another preferred embodiment, the α2M preparation comprises α2M complexed to antigenic peptides of the infected cells from which they are derived.

Also encompassed by the invention are methods of treatment and delivery, pharmaceutical compositions and formulas comprising administering at least one non-vaccine therapeutic modality and an HSP preparation or an α2M preparation and kits comprising such pharmaceutical compositions.

4. DESCRIPTION OF THE FIGURE

FIG. 1. Synopsis of clinical protocol described in section 7, infra. The synopsis includes all physical examinations, blood work, x-rays and bone marrow tests that were done before, during and after HSP-peptide complex vaccination.

5. DETAILED DESCRIPTION OF INVENTION

The present invention is based, in part, on the recognition that an HSP preparation can enhance or improve the therapeutic benefit of non-vaccine treatment modalities or therapeutic modalities for treatment of cancer or infectious diseases. Thus, the present invention encompasses methods and compositions that comprise administering an HSP preparation in combination with a non-vaccine treatment modality. Also encompassed are methods and compositions that comprise administering an α2M preparation in combination with a non-vaccine treatment modality. In particular, the invention encompasses methods of treatment and compositions that provide a better therapeutic profile than that of an HSP preparation or α2M preparation administered alone or a non-vaccine treatment modality administered alone. The source of the HSP or α2M is preferably an eukaryote, and most preferably a mammal. The subject receiving the treatment is preferably a mammal including, but not limited to, domestic animals, such as cats and dogs; wild animals, including foxes and raccoons; livestock and fowl, including horses, cattle, sheep, turkeys and chickens, as well as any rodents. Most preferably, the subject is human.

The invention provides methods for improving the therapeutic outcome of a non-vaccine treatment modality comprising administering either an HSP preparation or an α2M preparation, preferably a purified HSP preparation or a purified α2M preparation, in conjunction with the administration of the treatment modality. Either the HSP preparation or the α2M preparation can be administered over a period of time which may precede, overlap, and/or follow a treatment regimen with a non-vaccine treatment modality. The HSP preparation or the α2M preparation can be administered concurrently, before, or after the administration of the treatment modality. Examples of treatment modalities include but are not limited to antibiotics, antivirals, antifungal compounds, anti-cancer treatments such as chemotherapeutic agents, and radiation, as well as biological therapeutic agents and immunotherapeutic agents. In preferred embodiments, the treatment modality is useful in the treatment or prevention of cancer. In another preferred embodiment, the treatment modality is Gleevec™.

In one embodiment, the invention encompasses methods of treatment that provide better therapeutic profiles than the administration of the treatment modality or the HSP preparation alone. In another embodiment, the invention encompasses methods of treatment that provide better therapeutic profiles than the administration of the treatment modality or the α2M preparation alone. Encompassed by the invention are methods wherein the administration of a treatment modality with an HSP preparation or an α2M preparation has additive potency or additive therapeutic effect. The invention also encompasses synergistic outcomes where the therapeutic efficacy is greater than additive. Preferably, such administration of a treatment modality with an HSP preparation or with an α2M preparation also reduces or avoids unwanted or adverse effects. Given the invention, in certain embodiments, doses of non-vaccine treatment modality can be reduced or administered less frequently, preferably increasing patient compliance, improving therapy and/or reducing unwanted or adverse effects. In a specific embodiment, lower or less frequent doses of chemotherapy or radiation therapy are administered to reduce or avoid unwanted effects. Alternatively, doses of HSP preparation and doses of α2M preparation can be reduced or administered less frequently if administered with a treatment modality.

In one embodiment, the present invention provides a method for improving the outcome of a treatment in a subject receiving a therapeutic modality which is not a vaccine. The method comprises administering either a heat shock protein preparation, preferably a purified HSP preparation, or an α2M preparation, preferably a purified α2M preparation, to the subject before, concurrently with, or after the administration of the therapeutic modality. In a specific embodiment, the HSP preparation or the α2M preparation can augment the therapeutic benefit of a treatment modality and improve the outcome of the treatment. Without being bound by any theory or mechanism, the administration of a mammalian HSP preparation or α2M preparation to a subject can enhance the responsiveness of non-specific immune mechanisms of the subject, for example, by increasing the number of natural killer (NK) cells and/or accelerating the maturation of dendritic cells and/or can also enhance the responsiveness of specific immune mechanisms, such as by increasing the number of CD4+ and CD8+ T cells. In a specific embodiment, the HSP preparation is administered before the administration of the therapeutic modality. In another specific embodiment, the therapeutic modality is administered before the administration of the HSP preparation. In specific embodiment, the α2M preparation is administered before the administration of the therapeutic modality. In another specific embodiment, the therapeutic modality is administered before the administration of the α2M preparation.

In another embodiment, the present invention provides a method for improving the outcome of a treatment in a subject receiving an HSP preparation, preferably a purified HSP preparation, by administering a non-vaccine therapeutic modality to the subject before, concurrently with, or after the administration of the HSP preparation. In a specific embodiment, the non-vaccine therapeutic modality can augment the therapeutic benefit of an HSP preparation and improve the outcome of the treatment.

In another embodiment, the present invention provides a method for improving the outcome of a treatment in a subject receiving an α2M preparation, preferably a purified α2M preparation, by administering a non-vaccine therapeutic modality to the subject before, concurrently with, or after the administration of the α2M preparation. In a specific embodiment, the non-vaccine therapeutic modality can augment the therapeutic benefit of an α2M preparation and improve the outcome of the treatment.

In certain embodiments, the administration of the HSP/α2M preparation in the absence of administration of the therapeutic modality or the administration of the therapeutic modality in the absence of administration of the HSP/α2M preparation is not therapeutically effective. In a specific embodiment, the amount of HSP/α2M preparation or therapeutic modality is administered in an amount insufficient to be therapeutically effective alone. In alternate embodiments, both or at least one of the HSP/α2M preparation or therapeutic modality is therapeutically effective when administered alone.

In various embodiments, the methods comprise the administration of an HSP preparation, preferably a purified HSP preparation, to a subject receiving a treatment modality for the treatment of cancer or infectious diseases. Preferably the HSP preparation comprises HSP-peptide complexes displaying the antigenicity of a tumor specific antigen or tumor associated antigen of the type of cancer or an antigen of an infectious agent, i.e., heat shock proteins complexed to antigenic peptides of the cancer cells or infected cells from which the complexes are obtained. Accordingly, in one embodiment, the specific immunogenicity of the HSP preparation derives from the peptide complexed to the HSP. In preferred embodiments, the HSP-peptide complexes are isolated from an antigen source such as cancer tissues or infected tissues. In the practice of the invention, such HSP-peptide complexes are preferably, autologous to the individual subject, i.e., obtained from the tissues of the subject receiving the administration of HSP preparation and treatment modality, but need not be (i.e., allogeneic to the individual subject).

In various other embodiments, the methods comprise the administration of an α2M preparation, preferably a purified α2M preparation, to a subject receiving a treatment modality for the treatment of cancer or infectious diseases. Preferably the α2M preparation comprises α2M-peptide complexes displaying the antigenicity of a tumor specific antigen or tumor associated antigen of the type of cancer or an antigen of an infectious agent, i.e., α2M complexed to antigenic peptides of the cancer cells or infected cells from which the complexes are obtained. Accordingly, in one embodiment, the specific immunogenicity of the α2M preparation derives from the peptide complexed to the α2M. In preferred embodiments, the α2M-peptide complexes are isolated from an antigen source such as cancer tissues or infected tissues. In the practice of the invention, such α2M-peptide complexes are preferably, autologous to the individual subject, i.e., obtained from the tissues of the subject receiving the administration of α2M preparation and treatment modality, but need not be (i.e., allogeneic to the individual subject).

In one embodiment, the methods comprise the administration of an HSP preparation or an α2M preparation, preferably a purified HSP preparation or a purified α2M preparation, to a subject receiving a treatment modality for treatment of an infectious disease. Such treatment modalities are known in the art and include but are not limited to antibiotics, antivirals, antifungals as well as biological and immunotherapeutic agents. Preferably the HSP preparation comprises HSP-peptide complexes which display the antigenicity of an agent of the infectious disease. Preferably the α2M preparation comprises α2M-peptide complexes which display the antigenicity of an agent of the infectious disease. In a specific embodiment, the outcome of a treatment of a type of infectious disease in a subject receiving a non-vaccine therapeutic modality is improved by administering HSP-peptide complexes comprising an HSP complexed to a peptide that displays the antigenicity of an antigen of an agent of said type of infectious disease. Preferably, the HSP-peptide complexes are not present in admixture with HSP or α2M that is not complexed to a peptide that displays the antigenicity of an antigen of an agent of the same infectious disease. (See International Application No. PCT/US01/28840, filed Sep. 15, 2001). In one embodiment, the HSP preparation is administered prior to administration of the therapeutic modality. In another embodiment, the therapeutic modality is administered prior to administration of the HSP preparation. In another specific embodiment, the outcome of a treatment of a type of infectious disease in a subject receiving a non-vaccine therapeutic modality is improved by administering α2M-peptide complexes comprising an α2M complexed to a peptide that displays the antigenicity of an antigen of an agent of said type of infectious disease. Preferably, the α2M-peptide complexes are not present in admixture with HSP or α2M that is not complexed to a peptide that displays the antigenicity of an antigen of an agent of the same infectious disease. Preferably, the α2M preparation is administered prior to administration of the therapeutic modality.

In another embodiment, the methods comprise the administration of either an HSP preparation or an α2M preparation, preferably a purified HSP preparation or a purified α2M preparation, to a subject receiving a treatment modality for treatment of cancer. Such treatment modalities include but are not limited to anti-cancer therapies such as chemotherapies and radiation therapies as well as hormonal therapies, biological therapies and immunotherapies. In the methods of the invention the anti-cancer agents that can be used include but are not limited to cytotoxic agents, antimitotic agents, tubulin stabilizing agents, microtubule formation inhibiting agents, topoisomerase active agents, alkylating agents, DNA interactive agents, antimetabolites, RNA/DNA antimetabolites, and DNA antimetabolites. Preferably, the anti-cancer agent is a chemotherapeutic agent. Preferably the HSP preparation or α2M preparation is administered to a subject receiving a chemotherapy or radiation therapy for treatment of cancer. Preferably the HSP preparation comprises HSP-peptide complexes which display the antigenicity of the type of cancer being treated. Preferably where the preparation is an α2M preparation, the α2M preparation comprises α2M-peptide complexes which display the antigenicity of the type of cancer being treated. Accordingly, in preferred embodiments, the invention provides methods for improving the outcome of cancer treatment in a subject receiving a therapeutic modality which is not a vaccine using HSP-peptide complexes comprising an HSP complexed to a peptide that displays the antigenicity of a tumor specific antigen or tumor associated antigen of a type of cancer or using α2M-peptide complexes comprising an α2M complexed to a peptide that displays the antigenicity of a tumor specific antigen or tumor associated antigen of a type of cancer. In certain preferred embodiments, such HSP-peptide complexes and α2M-peptide complexes are not diluted with either HSP or α2M that is not complexed to a peptide that displays the antigenicity of an antigen of the same type of cancer. Preferably, the HSP preparation or α2M preparation is administered prior to administration of the therapeutic modality.

In a specific embodiment, an HSP preparation is administered to a subject receiving a chemotherapeutic agent for treatment of cancer. In another preferred embodiment, an α2M preparation is administered to a subject receiving a chemotherapeutic agent for treatment of cancer. Such chemotherapeutic agents are known in the art and include but are not limited to: methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, doxorubicin, epirubicin, 5-fluorouracil, taxanes such as docetaxel and paclitaxel, leucovorin, levamisole, irinotecan, estramustine, etoposide, nitrosoureas such as carmustine and lomustine, vinca alkaloids, platinum compounds, mitomycin, gemcitabine, hexamethylmelamine, topotecan, tyrosine kinase inhibitors, tyrphostins, Gleevec™ (imatinib mesylate), herbimycin A, genistein, erbstatin, and lavendustin A. In a preferred embodiment, the chemotherapeutic agent is Gleevec™ (imatinib mesylate).

In other embodiments, suitable chemotherapeutics include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, the anti-cancer agent can be, but is not limited to, a drug listed in Table 1.

TABLE 1

| Alkylating agents | |
|---|---|
| Nitrogen mustards: | Cyclophosphamide |
|  | Ifosfamide |
|  | Trofosfamide |
|  | Chlorambucil |
| Nitrosoureas: | Carmustine (BCNU) |
|  | Lomustine (CCNU) |
| Alkylsulphonates: | Busulfan |
|  | Treosulfan |
| Triazenes: | Dacarbazine |
| Platinum containing | Cisplatin |
| compounds: | Carboplatin |
|  | Aroplatin |
|  | Oxaliplatin |
| Plant Alkaloids | |
| Vinca alkaloids: | Vincristine |
|  | Vinblastine |
|  | Vindesine |
|  | Vinorelbine |
| Taxoids: | Paclitaxel |
|  | Docetaxel |
| DNA Topoisomerase Inhibitors | |
| Epipodophyllins: | Etoposide |
|  | Teniposide |
|  | Topotecan |
|  | 9-aminocamptothecin |
|  | Camptothecin |
|  | Crisnatol |

TABLE 1-continued

| mitomycins: | Mitomycin C |
|---|---|
| Anti-metabolites | |
| Anti-folates: | |
| DHFR inhibitors: | Methotrexate |
|  | Trimetrexate |
| IMP dehydrogenase | Mycophenolic acid |
| Inhibitors: | Tiazofurin |
|  | Ribavirin |
|  | EICAR |
| Ribonucleotide reductase | Hydroxyurea |
| Inhibitors: | Deferoxamine |
| Pyrimidine analogs: | |
| Uracil analogs: | 5-Fluorouracil |
|  | Floxuridine |
|  | Doxifluridine |
|  | Ratitrexed |
| Cytosine analogs: | Cytarabine (ara C) |
|  | Cytosine arabinoside |
|  | Fludarabine |
| Purine analogs: | Mercaptopurine |
|  | Thioguanine |
| DNA Antimetabolites: | 3-HP |
|  | 2'-deoxy-5-fluorouridine |
|  | 5-HP |
|  | alpha-TGDR |
|  | aphidicolin glycinate |
|  | ara-C |
|  | 5-aza-2'-deoxycytidine |
|  | beta-TGDR |
|  | cyclocytidine |
|  | guanazole |
|  | inosine glycodialdehyde |
|  | macebecin II |
|  | pyrazoloimidazole |
| Hormonal therapies: | |
| Receptor antagonists: | |
| Anti-estrogen: | Tamoxifen |
|  | Raloxifene |
|  | Megestrol |
| LHRH agonists: | Goscrelin |
|  | Leuprolide acetate |
| Anti-androgens: | Flutamide |
|  | Bicalutamide |
| Retinoids/Deltoids | |
|  | Cis-retinoic acid |
| Vitamin A derivative: | All-trans retinoic acid (ATRA-IV) |
| Vitamin D3 analogs: | EB 1089 |
|  | CB 1093 |
|  | KH 1060 |
| Photodynamic therapies: | Vertoporfin (BPD-MA) |
|  | Phthalocyanine |
|  | Photosensitizer Pc4 |
|  | Demethoxy-hypocrellin A |
|  | (2BA-2-DMHA) |
| Cytokines: | Interferon-α |
|  | Interferon-γ |
|  | Tumor necrosis factor |
| Angiogenesis Inhibitors: | Angiostatin (plasminogen fragment) |
|  | antiangiogenic antithrombin III |
|  | Angiozyme |
|  | ABT-627 |
|  | Bay 12-9566 |
|  | Benefin |
|  | Bevacizumab |
|  | BMS-275291 |
|  | cartilage-derived inhibitor (CDI) |
|  | CAI |
|  | CD59 complement fragment |
|  | CEP-7055 |
|  | Col 3 |
|  | Combretastatin A-4 |
|  | Endostatin (collagen XVIII fragment) |
|  | Fibronectin fragment |
|  | Gro-beta |
|  | Halofuginone |
|  | Heparinases |

TABLE 1-continued

| | |
|---|---|
| | Heparin hexasaccharide fragment |
| | HMV833 |
| | Human chorionic gonadotropin (hCG) |
| | IM-862 |
| | Interferon alpha/beta/gamma |
| | Interferon inducible protein (IP-10) |
| | Interleukin-12 |
| | Kringle 5 (plasminogen fragment) |
| | Marimastat |
| | Metalloproteinase inhibitors (TIMPs) |
| | 2-Methoxyestradiol |
| | MMI 270 (CGS 27023A) |
| | MoAb IMC-1C11 |
| | Neovastat |
| | NM-3 |
| | Panzem |
| | P1-88 |
| | Placental ribonuclease inhibitor |
| | Plasminogen activator inhibitor |
| | Platelet factor-4 (PF4) |
| | Prinomastat |
| | Prolactin 16 kD fragment |
| | Proliferin-related protein (PRP) |
| | PTK 787/ZK 222594 |
| | Retinoids |
| | Solimastat |
| | Squalamine |
| | SS 3304 |
| | SU 5416 |
| | SU6668 |
| | SU11248 |
| | Tetrahydrocortisol-S |
| | tetrathiomolybdate |
| | thalidomide |
| | Thrombospondin-1 (TSP-1) |
| | TNP-470 |
| | Transforming growth factor-beta (TGF-b) |
| | Vasculostatin |
| | Vasostatin (calreticulin fragment) |
| | ZD6126 |
| | ZD 6474 |
| | farnesyl transferase inhibitors (FTI) |
| | bisphosphonates |
| Antimitotic agents: | allocolchicine |
| | Halichondrin B |
| | colchicine |
| | colchicine derivative |
| | dolstatin 10 |
| | maytansine |
| | rhizoxin |
| | thiocolchicine |
| | trityl cysteine |
| | Others: |
| | Isoprenylation inhibitors: |
| Dopaminergic neurotoxins: | 1-methyl-4-phenylpyridinium ion |
| Cell cycle inhibitors: | Staurosporine |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | Verapamil |
| $Ca^{2+}$ATPase inhibitors: | Thapsigargin |

Additional anti-cancer agents that may be used in the methods of the present invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs that can be used include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine;

betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic plaxinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-sap orin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred chemotherapeutics of the invention include Gleevec™ (imatinib mesylate) and other tyrosine kinase inhibitors.

In preferred embodiments, each of the methods above comprise administering either an HSP preparation or an α2M preparation, preferably a purified HSP preparation or a purified α2M preparation, to a subject receiving a drug of the 2-phenylaminopyrimidine class for treatment of cancer. More preferably, the subject is receiving Gleevec™ (i.e., imatinib mesylate) for treatment of cancer.

In another preferred embodiment, an HSP preparation or an α2M preparation is administered to a subject receiving radiation therapy for treatment of cancer. For radiation treatment, the radiation can be gamma rays or X-rays. The methods encompass treatment of cancer comprising radiation therapy, such as external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J.B. Lippencott Company, Philadelphia. In preferred embodiments, the radiation treatment is administered as external beam radiation or teletherapy wherein the radiation is directed from a remote source. In various preferred embodiments, the radiation treatment is administered as internal therapy or brachytherapy wherein a radioactive source is placed inside the body close to cancer cells or a tumor mass.

In another embodiment, the each of the above methods comprise the administration of HSP preparation, preferably a purified HSP preparation, to a subject receiving a combination of treatment modalities for the treatment of cancer. In another embodiment, the each of the above methods comprise the administration of an α2M preparation, preferably a purified α2M preparation, to a subject receiving a combination of treatment modalities for the treatment of cancer. Preferably the HSP preparation and α2M preparation each comprises HSP-peptide complexes and α2M-peptide complexes, respectively, which display the antigenicity of the type of cancer being treated. In one such embodiment, HSP preparation is administered to a subject receiving a chemotherapy in combination with a biological therapy, preferably a cytokine. In another such embodiment, an α2M preparation is administered to a subject receiving a chemotherapy in combination with a biological therapy, preferably a cytokine. In various embodiments, the cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, TNFα, TNFβ, G-CSF, GM-CSF, TGF-β, IL-15, IL-18, GM-CSF, INF-γ, INF-α, SLC, endothelial monocyte activating protein-2 (EMAP2), MIP-3α, MIP-3β, or an MHC gene, such as HLA-β7. Additionally, other exemplary cytokines include other members of the TNF family, including but not limited to TNF-α-related apoptosis-inducing ligand (TRAIL), TNF-α-related activation-induced cytokine (TRANCE), TNF-α-related weak inducer of apoptosis (TWEAK), CD40 ligand (CD40L), LT-α, LT-β, OX40L, CD40L, FasL, CD27L, CD30L, 4-1BBL, APRIL, LIGHT, TL1, TNFSF16, TNFSF17, and AITR-L, or a functional portion thereof. See, e.g., Kwon et al., 1999, Curr. Opin. Immunol. 11:340-345 for a general review of the TNF family. Preferably, the HSP preparation is administered prior to the treatment modalities.

In a specific embodiment, a purified HSP preparation is administered to a subject receiving cyclophosphamide in combination with IL-12 for treatment of cancer. In another specific embodiment, a purified α2M preparation is administered to a subject receiving cyclophosphamide in combination with IL-12 for treatment of cancer.

In another specific embodiment, the chemotherapeutic is a tyrosine kinase inhibitor, the HSP preparation is obtained from the cancer subject being treated, and the chemotherapy is administered prior to administration of the HSP preparation. In another specific embodiment, the anti-cancer agent is the chemotherapeutic Gleevec™ (imatinib mesylate), the HSP preparation comprises hsp70 obtained from the cancer subject being treated, and the chemotherapeutic is administered prior to administration of the HSP preparation. In another specific embodiment, the HSP preparation comprises hsp70-peptide complexes obtained from the cancer subject being treated. Another specific embodiment encompasses a method for treating CML in a subject receiving about 400 mg to 800 mg of imatinib mesylate daily comprising administering a heat shock protein preparation to said subject, wherein said heat shock protein preparation comprises hsp70 peptide complexes. In preferred embodiments, the heat shock protein preparation is administered once a week and the heat shock protein preparation comprises hsp70-peptide complexes obtained from said subject.

In certain specific embodiments, an HSP preparation is administered to a subject already receiving Gleevec™ (e.g., 400-800 mg daily in capsule form, 400-600 mg doses administered once daily, or 800 mg dose administered daily in two doses of 400 mg each). In such embodiments, an HSP/α2M preparation is initially administered to a subject who has already been receiving Gleevec™ in the absence of HSP/α2M preparation 2 days, 2 days to 1 week, 1 week to 1 month, 1 month to 6 months, 6 months to 1 year prior to administration of HSP/α2M preparation in addition to Gleevec™. In a specific embodiment, an HSP/α2M preparation is administered to a subject wherein the subject showed resistance to treatment with Gleeve™ alone.

In other embodiments, an HSP/α2M preparation is initially administered to a subject concurrently with the initial administration of Gleevec™.

In yet other specific embodiments, Gleevec™ (e.g., 400-800 mg daily in capsule form) is administered to a subject already receiving treatment comprising administration of an HSP/α2M preparation. In such embodiments, Gleevec™ is initially administered to a subject who has already been receiving an HSP/α2M preparation in the absence of Gleevec™ 2 days, 2 days to 1 week, 1 week to 1 month, 1 month to 6 months, 6 months to 1 year prior to administration of Gleevec™ in addition to administration of an HSP/α2M preparation, In a specific embodiment, Gleevec™ is administered orally. In another specific embodiment, the HSP preparation is administered intradermally.

In each of the methods contemplated above, the patient, by way of example, receives 50 mg to 100 mg, 100 mg to 200 mg, 200 mg to 300 mg, 300 mg to 400 mg, 400 mg to 500 mg, 500 mg to 600 mg, 600 mg to 700 mg, 700 mg to 800 mg, 800 mg to 900 mg, or 900 mg to 1000 mg of Gleevec™ daily. In certain embodiments, the total daily dose is administered to a subject as two daily doses of 25 mg to 50 mg, 50 mg to 100 mg, 100 mg to 200 mg, 200 mg to 300 mg, 300 mg to 400 mg, or 400 mg to 500 mg.

Other treatment modalities contemplated include but are not limited to antiviral agents known in the art. Such antiviral agents include but are not limited to: ribavirin, rifampicin, AZT, ddI, ddC, acyclovir and ganciclovir.

Also encompassed by the invention are therapeutic modalities that are antibiotic agents known in the art including but not limited to: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g. clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g. furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Also encompassed by the invention are therapeutic modalities that are antifungal agents and known in the art and include but are not limited to: polyenes (e.g., amphotericin b, candicidin, mepartricin, natamycin, and nystatin), allylamines (e.g., butenafine, and naftifine), imidazoles (e.g., bifonazole, butoconazole, chlordantoin, flutrimazole, isoconazole, ketoconazole, and lanoconazole), thiocarbamates (e.g, tolciclate, tolindate, and tolnaftate), triazoles (e.g., fluconazole, itraconazole, saperconazole, and terconazole), bromosalicylchloranilide, buclosamide, calcium propionate, chlorphenesin, ciclopirox, azaserine, griseofulvin, oligomycins, neomycin undecylenate, pyrrolnitrin, siccanin, tubercidin, and viridin.

In another embodiment, the above methods are useful for the prevention of cancer or infectious disease. In a specific embodiment, an HSP preparation is administered in conjunction with a non-vaccine treatment modality to a subject to reduce the risk of acquiring a type of cancer or an infectious disease. In other specific embodiments, the methods encompass administration of an HSP preparation with administration of a non-vaccine treatment modality as a preventative measure to a subject having a genetic or non-genetic predisposition to a cancer or infectious disease or to a subject facing exposure to an agent of an infectious disease. In further embodiments, the invention also provides that each of the foregoing embodiments also can be applicable wherein an α2M preparation is administered in conjunction with a non-vaccine treatment modality.

The methods and compositions of the invention are useful not only in untreated patients, but are also useful in the treatment of patients partially or completely unresponsive to the therapeutic modality in the absence of the HSP/α2M preparation or to the HSP/α2M preparation in the absence of the therapeutic modality. In various embodiments, the invention provides methods and compositions useful in the treatment or prevention of diseases and disorders in patients that have been shown to be or may be refractory or nonresponsive to therapies comprising the administration of either or both the HSP/α2M preparation or the therapeutic modality. The invention also includes methods and compositions comprising administration of the HSP/α2M preparation and the therapeutic modality to patients that have previously received and/or are concurrently receiving other forms of medical therapy.

The HSP preparation used in the methods and compositions of the invention is preferably purified, and can include free HSP not bound to any molecule, and molecular complexes of HSP with another molecule, such as a peptide. An HSP-peptide complex comprises an HSP covalently or non-covalently attached to a peptide. The methods of the invention may or may not require covalent or noncovalent attachment of an HSP to any specific antigens or antigenic peptides prior to administration to a subject. Although, the peptide(s) may be unrelated to the infectious disease or disorder or particular cancer being treated, in preferred embodiments, the HSP preparation comprises complexes which display the antigenicity of an antigen of the agent of infectious disease or of a tumor specific antigen or tumor associated antigen of the type of cancer being treated, respectively. More preferably, for the treatment of infectious disease, the HSP preparation comprises noncovalent HSP-peptide complexes isolated from a cell infected with an infectious agent (or non-infectious variant thereof displaying the antigenicity thereof) that causes the infectious disease. More preferably, for treatment of a type of cancer, the HSP preparation comprises noncovalent HSP-peptide complexes isolated from cancerous tissue of said type of cancer or a metastasis thereof, which can be from the patient (autologous) or not (allogeneic). Accordingly, for the purposes of this invention, an HSP preparation is a composition comprising HSPs whether unbound or bound to other molecules (e.g., peptides). The HSP is preferably purified. An HSP preparation may include crude cell lysate comprising HSP, the amount of lysate corresponding to between 100 to $10^8$ cell equivalents. HSPs can be conveniently purified from most cellular sources as a population of complexes of different peptides non-covalently bound to HSPs. The HSPs can be separated from the non-covalently bound peptides by exposure to low pH and/or adenosine triphosphate, or other methods known in the art.

The α2M preparation used in the methods and compositions of the invention is preferably purified, and can include free α2M not bound to any molecule, and molecular complexes of α2M with another molecule, such as a peptide. An α2M-peptide complex comprises an α2M covalently or non-covalently attached to a peptide. The methods of the invention may or may not require covalent or noncovalent attachment of an α2M to any specific antigens or antigenic peptides prior to administration to a subject. Although, the peptide(s) may be unrelated to the infectious disease or disorder or particular cancer being treated, in preferred embodiments, the α2M preparation comprises complexes which display the antigenicity of an antigen of the agent of infectious disease or of a tumor specific antigen or tumor associated antigen of the type of cancer being treated, respectively. More preferably, for the treatment of infectious disease, the α2M preparation comprises noncovalent α2M-peptide complexes isolated from a cell infected with an infectious agent (or non-infectious variant thereof displaying the antigenicity thereof) that causes the infectious disease. More preferably, for treatment of a type of cancer, the α2M preparation comprises noncovalent α2M-peptide complexes isolated from cancerous tissue of said type of cancer or a metastasis thereof, which can be from the patient (autologous) or not (allogeneic). Accordingly, for the purposes of this invention, an α2M preparation is a composition comprising α2M whether unbound or bound to other molecules (e.g., peptides). The α2M is preferably purified. An α2M preparation may include crude cell lysate comprising α2M, the amount of lysate corresponding to between 100 to $10^8$ cell equivalents. α2M s can be conveniently purified from most cellular sources as a population of complexes of different peptides non-covalently bound to α2Ms. The α2M can be separated from the non-covalently bound peptides by exposure to low pH and/or adenosine triphosphate, or other methods known in the art.

In various embodiments, the source of the HSP and the α2M is preferably an eukaryote, more preferably a mammal, and most preferably a human. Accordingly, the HSP preparation used by the methods of the invention includes eukaryotic HSPs, mammalian HSPs and human HSPs. The α2M preparation includes eukaryotic α2M, mammalian α2M and human α2M. The eukaryotic source from which the HSP preparation or α2M preparation is derived and the subject receiving the HSP preparation or the α2M preparation, respectively, are preferably the same species.

In one embodiment, the specific immunogenicity of the HSP preparation derives from the peptide complexed to a heat shock protein. Accordingly, in various embodiments, the HSP preparation comprises heat shock protein peptide complexes wherein the heat shock proteins are complexed to peptides derived from a specific antigen source. In a preferred embodiment, the HSP protein preparation comprises heat shock protein-peptide complexes that are autologous. In another preferred embodiment, the HSP preparation comprises heat shock proteins complexed to antigenic peptides of the cancer cells from which they are derived. In specific embodiments, the antigen is a tumor specific antigen (i.e., only expressed in the tumor cells). In other specific embodiments, the antigen is a tumor associated antigen (i.e., relatively overexpressed in the tumor cells). In yet another preferred embodiment, the HSP preparation comprises heat shock proteins complexed to antigenic peptides of the infected cells from which they are derived.

In another embodiment, the specific immunogenicity of the α2M preparation derives from the peptide complexed to an α2M. Accordingly, in various embodiments, the α2M preparation comprises α2M peptide complexes wherein the α2M are complexed to peptides derived from a specific antigen source. In a preferred embodiment, the α2M protein preparation comprises α2M-peptide complexes that are autologous. In another preferred embodiment, the α2M preparation comprises α2M complexed to antigenic peptides of the cancer cells from which they are derived. In other specific embodiments, the antigen is a tumor associated antigen (i.e., relatively overexpressed in the tumor cells). In yet another preferred embodiment, the α2M preparation comprises α2M complexed to antigenic peptides of the infected cells from which they are derived.

In various specific embodiments, the above methods comprise the administration of HSP preparation or α2M preparation to a subject treated with a treatment modality wherein the treatment modality administered alone is not clinically adequate to treat the subject such that the subject needs additional effective therapy, e.g., a subject is unresponsive to a treatment modality without administering HSP preparation or α2M preparation. Included in such embodiments are methods comprising administering HSP preparation or α2M preparation to a subject receiving a treatment modality wherein said subject has responded to therapy yet suffers from side effects, relapse, develops resistance, etc. Such a subject might be non-responsive or refractory to treatment with the treatment modality alone. The embodiments provide that the methods of the invention comprising administration of HSP preparation to a subject refractory to a treatment modality alone can improve the therapeutic effectiveness of the treatment modality when administered as contemplated by the methods of the invention. The methods of the invention comprising administration of an α2M preparation to a subject refractory to a treatment modality alone can also improve the therapeutic effectiveness of the treatment modality when administered as contemplated by the methods of the invention.

In a specific embodiment, an HSP preparation is administered to a subject receiving a treatment modality for the treatment of cancer wherein the subject may be non-responsive or refractory to treatment with the treatment modality alone, i.e., at least some significant portion of cancer cells are not killed or their cell division is not arrested. The determination of the effectiveness of a treatment modality can be assayed in vivo or in vitro using methods known in the art. Art-accepted meanings of refractory are well known in the context of cancer. In one embodiment, a cancer is refractory or non-responsive where the number of cancer cells has not been significantly reduced, or has increased. In a preferred embodiment, an HSP preparation that displays the antigenicity of a type of cancer is administered to a subject non-responsive to administration of a treatment modality alone, wherein the administration of HSP preparation improves the effectiveness of the treatment modality. Among these subjects being treated are those receiving chemotherapy or radiation therapy.

In a specific embodiment, an α2M preparation is administered to a subject receiving a treatment modality for the treatment of cancer wherein the subject may be non-responsive or refractory to treatment with the treatment modality alone, i.e., at least some significant portion of cancer cells are not killed or their cell division is not arrested. The determination of the effectiveness of a treatment modality can be assayed in vivo or in vitro using methods known in the art. Art-accepted meanings of refractory are well known in the context of cancer. In one embodiment, a cancer is refractory or non-responsive where the number of cancer cells has not been significantly reduced, or has increased. In a preferred embodiment, an α2M preparation that displays the antigenicity of a type of cancer is administered to a subject non-responsive to administration of a treatment modality alone, wherein the administration of α2M preparation improves the effectiveness of the treatment modality. Among these subjects being treated are those receiving chemotherapy or radiation therapy.

In a specific embodiment, an HSP preparation is administered to a subject receiving a treatment modality for the treatment of cancer wherein the subject may experience unwanted or adverse effects to treatment with the treatment modality alone, e.g., the treatment modality may be toxic or harmful at its effective dose, administered alone. Given the invention, the HSP preparation can improve the therapeutic benefit of the treatment modality such that the dosage or frequency of administration of the treatment modality can be lowered when administered in conjunction with HSP preparation. In a preferred embodiment, an HSP preparation that displays the antigenicity of a type of cancer is administered to a subject to reduce or avoid the unwanted or adverse effects of a treatment modality alone, wherein the administration of HSP preparation allows lower and/or less frequent doses of the treatment modality. Among these subjects being treated are those receiving chemotherapy or radiation therapy.

In a specific embodiment, an α2M preparation is administered to a subject receiving a treatment modality for the treatment of cancer wherein the subject may experience unwanted or adverse effects to treatment with the treatment modality alone, e.g., the treatment modality may be toxic or harmful at its effective dose, administered alone. Given the invention, the α2M preparation can improve the therapeutic benefit of the treatment modality such that the dosage or frequency of administration of the treatment modality can be lowered when administered in conjunction with α2M preparation. In a preferred embodiment, an α2M preparation that displays the antigenicity of a type of cancer is administered to a subject to reduce or avoid the unwanted or adverse effects of a treatment modality alone, wherein the administration of α2M preparation allows lower and/or less frequent doses of the treatment modality. Among these subjects being treated are those receiving chemotherapy or radiation therapy.

In a specific embodiment, the HSP preparation is administered in a sub-optimal amount, e.g., an amount that does not manifest detectable therapeutic benefits when administered in the absence of the therapeutic modality, as determined by methods known in the art. In such methods, the administration of such a sub-optimal amount of HSP preparation to a subject receiving a therapeutic modality results in an overall improvement in effectiveness of treatment. In another specific embodiment, the α2M preparation is administered in a sub-optimal amount. In such methods, the administration of such a sub-optimal amount of α2M preparation to a subject receiving a therapeutic modality results in an overall improvement in effectiveness of treatment.

In a preferred embodiment, an HSP preparation is administered in an amount that does not result in tumor regression or cancer remission or an amount wherein the cancer cells have not been significantly reduced or have increased when said HSP preparation is administered in the absence of the therapeutic modality. Preferably the HSP preparation comprises HSP-peptide complexes displaying the antigenicity of the cancer type being treated. In a preferred embodiment, the sub-optimal amount of HSP preparation is administered to a subject receiving a treatment modality whereby the overall effectiveness of treatment is improved. In another preferred embodiment, an α2M preparation is administered in an amount that does not result in tumor regression or cancer remission or an amount wherein the cancer cells have not been significantly reduced or have increased when said α2M preparation is administered in the absence of the therapeutic modality. Preferably the α2M preparation comprises α2M-peptide complexes displaying the antigenicity of the cancer type being treated. In a preferred embodiment, the sub-optimal amount of α2M preparation is administered to a subject receiving a treatment modality whereby the overall effectiveness of treatment is improved. Among these subjects being treated with HSP or α2M preparation are those receiving chemotherapy or radiation therapy. A sub-optimal amount can be determined by appropriate animal studies. Such a sub-optimal amount in humans can be determined by extrapolation from experiments in animals.

The HSP preparation or α2M preparation can be administered prior to, concurrently with, or subsequent to the administration of the non-vaccine treatment modality. In one embodiment, the HSP preparation and therapeutic modality are administered at exactly the same time. In another embodiment, the α2M preparation and therapeutic embodiment are administered at exactly the same time. In another embodiment the either the HSP, preparation or the α2M preparation and treatment modality are administered in a sequence and within a time interval such that the HSP preparation and treatment modality can act together to provide an increased benefit than if they were administered alone or such that the α2M preparation and treatment modality can act together to provide an increased benefit than if they were administered alone. In another embodiment, the HSP preparation and treatment modality are administered sufficiently close in time so as to provide the desired therapeutic outcome. In another embodiment, the α2M preparation and treatment modality are administered sufficiently close in time so as to provide the desired therapeutic outcome. The HSP or α2M preparation and the therapeutic modality can be administered simultaneously or separately, in any appropriate form and by any suitable route. In one embodiment, the HSP preparation and treatment modality are administered by different routes of administration. In an alternate embodiment, each is administered by the same route of administration. The HSP preparation can be administered at the same or different sites, e.g. arm and leg. In another embodiment, the α2M preparation and treatment modality are administered by different routes of administration. Alternatively, each can be administered by the same route. In addition, each could be administered at the same or different sites.

In various embodiments, such as those described above, the HSP preparation and treatment modality are administered less than 1 hour apart, at about 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart, or no more than 1 week or 2 weeks or 1 month or 3 months apart. In other embodiments, the HSP preparation and treatment modality are administered 2 to 4 days apart, 4 to 6 days apart, 1 week apart, 1 to 2 weeks apart, 2 to 4 weeks apart, one month apart, 1 to 2 months apart, or 2 or more months apart. In preferred embodiments, the HSP preparation and treatment modality are administered in a time frame where both are still active. One skilled in the art would be able to determine such a time frame by determining the half life of each administered component. In separate or in the foregoing embodiments, the HSP preparation and treatment modality are administered less than 2 weeks, one month, six months, 1 year or 5 years apart. Preferably, the HSP preparation is administered prior to the treatment modality. In further embodiments, the α2M preparation and treatment modality are administered at the time intervals and time frames described in each of the above embodiments. Preferably the α2M preparation is administered prior to the treatment modality. Preferably, in each of the above embodiments, the treatment modality is a combination of a chemotherapy and cytokine treatment.

In one embodiment, the treatment modality is administered daily and the HSP preparation or α2M preparation is administered once a week for the first 4 weeks, and then once every other week thereafter. In one embodiment, the treatment modality is administered daily and the HSP preparation or α2M preparation is administered once a week for the first 8 weeks, and then once every other week thereafter.

In one embodiment, two or more components are administered within the same patient visit. In one embodiment, the α2M preparation is administered prior to the administration of the treatment modality. In an alternate embodiment, the α2M preparation is administered subsequent to the administration of the treatment modality. In one embodiment, the α2M preparation is administered prior to the administration of the treatment modality. In an alternate embodiment, the HSP preparation is administered subsequent to the administration of the treatment modality.

In certain embodiments, the HSP preparation or the α2M preparation and non-vaccine treatment modality are cyclically administered to a subject. Cycling therapy involves the administration of the HSP preparation for a period of time, followed by the administration of a treatment modality for a period of time and repeating this sequential administration. Alternatively, cycling therapy can involve the administration of α2M preparation for a period of time, followed by the administration of a treatment modality for a period of time and repeating this sequential administration. Cycling therapy can reduce the development of resistance to one or more of the therapies, avoid or reduce the side effects of one of the therapies, and/or improve the efficacy of the treatment. In such embodiments, the invention contemplates the alternating administration of an HSP preparation followed by the administration of a treatment modality 4 to 6 days later, preferable 2 to 4 days, later, more preferably 1 to 2 days later, wherein such a cycle may be repeated as many times as desired. The invention also contemplates the alternating administration of an α2M preparation followed by the administration of a treatment modality 4 to 6 days later, preferable 2 to 4 days, later, more preferably 1 to 2 days later, wherein such a cycle may be repeated as many times as desired.

In certain embodiments, the HSP preparation and treatment modality are alternately administered in a cycle of less than 3 weeks, once every two weeks, once every 10 days or once every week. In other embodiments, the α2M preparation and treatment modality are alternately administered in cycles of less than 3 weeks, once every two weeks, once every 10 days or once every week. In a specific embodiment of the invention, one cycle can comprise the administration of a chemotherapeutic by infusion over 90 minutes every cycle, 1 hour every cycle, or 45 minutes every cycle. Each cycle can comprise at least 1 week of rest, at least 2 weeks of rest, at least 3 weeks of rest. In an embodiment, the number of cycles administered is from 1 to 12 cycles, more typically from 2 to 10 cycles, and more typically from 2 to 8 cycles.

In a preferred embodiment, an HSP preparation displaying the antigenicity of a tumor specific or tumor associated antigen of a type of cancer is administered to a subject in an amount ineffective for treating said cancer about 2 weeks to 1 month prior to receiving combination chemotherapy with cytokine treatment, wherein treatment effectiveness is greater than the effectiveness of HSP preparation or combination chemotherapy with cytokine treatment administered alone. Preferably the subject is human. In a preferred embodiment, the subject is non-responsive to combination chemotherapy with cytokine treatment prior to administration of HSP preparation. In another preferred embodiment, the chemotherapy is cyclophosphamide, the cytokine is IL-12, and the HSP preparation comprises gp96-peptide complexes obtained from cancerous tissue of the subject.

In particularly preferred embodiment, an α2M preparation displaying the antigenicity of a tumor specific or tumor associated type of cancer is administered to a subject in an amount ineffective for treating said cancer about 2 weeks to 1 month prior to receiving combination chemotherapy with cytokine treatment, wherein treatment effectiveness is greater than the effectiveness of α2M preparation or combination chemotherapy with cytokine treatment administered alone. Preferably the subject is human. In a preferred embodiment, the subject is non-responsive to combination chemotherapy with cytokine treatment prior to administration of α2M preparation. In another preferred embodiment, the chemotherapy is cyclophosphamide, the cytokine is IL-12, and the α2M preparation comprises α2M-peptide complexes obtained from cancerous tissue of the subject.

In specific embodiments, the above methods encompass the administration of Gleevec™ (imatinib mesylate) for treatment of cancer. In a preferred embodiment, the cancer is CML, the chemotherapeutic is Gleevec™ (imatinib mesylate), and the HSP preparation comprises hsp70-peptide complexes obtained from the cancer subject being treated.

Also encompassed by the invention are methods of treatment and delivery, pharmaceutical compositions and formulas comprising administering at least one non-vaccine therapeutic modality and an HSP preparation or an α2M preparation and kits comprising such pharmaceutical compositions.

5.1. Heat Shock Protein Preparations

Three major families of HSPs have been identified based on molecular weight. The families have been called hsp60, hsp70 and hsp90 where the numbers reflect the approximate molecular weight of the stress proteins in kilodaltons. Many members of these families were found subsequently to be induced in response to other stressful stimuli including, but not limited to, nutrient deprivation, metabolic disruption, oxygen radicals and infection with intracellular pathogens (See Welch, May 1993, Scientific American 56-64; Young, 1990, Annu. Rev. Immunol. 8:401-420; Craig, 1993, Science 260:1902-1903; Gething, et al., 1992, Nature 355:33-45; and Lindquist, et al., 1988, Annu. Rev. Genetics 22:631-677). A number of proteins thought to be involved in chaperoning functions are residents of the endoplasmic reticulum (ER) lumen and include, for example, protein disulfide isomerase (PDI; Gething et al., 1992, Nature 355:33-45), calreticulin (Herbert et al., 1997, J. Cell Biol. 139:613-623), Grp94 or ERp99 (Sorger & Pelham, 1987, J. Mol. Biol. 194:(2) 341-4) which is related to hsp90, and Grp78 or BiP, which is related to hsp70 (Munro et al., 1986, Cell 46:291-300; Haas & Webl, 1983, Nature 306:387-389). It is contemplated that HSPs belonging to all of these three families, including fragments of such HSPs, can be used in the practice of the instant invention. It is also noted that HSPs include constitutively expressed conserved cellular homologs of the proteins induced by stress.

HSPs are also referred to interchangeably herein as stress proteins and can be selected from among any cellular protein that satisfies the following criteria. It is a protein whose intracellular concentration increases when a cell is exposed to a stressful stimuli, it is capable of binding other proteins or peptides, it is capable of releasing the bound proteins or peptides in the presence of adenosine triphosphate (ATP) or low pH, and it is a protein showing at least 35% homology with any cellular protein having any of the above properties.

Heat shock proteins are among the most highly conserved proteins in existence. For example, DnaK, the hsp70 from *E. coli* has about 50% amino acid sequence identity with hsp70 proteins from excoriates (Bardwell, et al., 1984, Proc. Natl. Acad. Sci. 81:848-852). The hsp60 and hsp90 families also show similarly high levels of intra families conservation (Hickey, et al., 1989, Mol. Cell. Biol. 9:2615-2626; Jindal, 1989, Mol. Cell. Biol. 9:2279-2283). In addition, it has been discovered that the hsp60, hsp70 and hsp90 families are composed of proteins that are related to the stress proteins in sequence, for example, having greater than 35% amino acid identity, but whose expression levels are not altered by stress. Therefore it is contemplated that stress proteins/HSPs include other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus. The purification of stress proteins belonging to these three families is described below.

In addition, HSPs have been found to have immunological and antigenic properties. HSPs are now understood to play an essential role in immune regulation. For instance, prior experiments have demonstrated that HSPs stimulate strong and long-lasting specific immune responses against antigenic peptides that have been covalently or noncovalently attached to the HSPs. By utilizing a specific peptide, the immune response generated is "specific" or targeted to that peptide.

Where HSP-peptide complexes are used in conjunction with administration of a non-vaccine treatment modality, preferably, the peptides are antigenic or relevant to the condition. In particular preferred embodiments, it is contemplated that the therapeutic outcome of a treatment modality administered to a subject with a particular type of cancer is improved by the administration of an HSP-peptide complex wherein the peptide displays the antigenicity of an antigen of that type of cancer.

In the present invention, an HSP preparation can include but not be limited to unbound hsp70, hsp90, gp96, calreticulin, hsp110 or grp170 or noncovalent or covalent complexes thereof complexed to a peptide.

5.2. Preparation of Heat Shock Proteins and α2M

In the present invention, purified unbound HSPs, HSPs covalently or noncovalently bound to specific peptides or nonspecific peptides (collectively referred to herein as HSP-peptide complexes), and combinations of thereof are used. Purification of HSPs in complexed or non-complexed forms are described in the following subsections. Further, one skilled in the art can synthesize HSPs by recombinant expression or peptide synthesis, which are also described below.

Also encompassed by the present invention are purified unbound α2M, α2M covalently or noncovalently bound to specific peptides or nonspecific peptides (collectively referred to herein as α2M-peptide complexes), and combinations of thereof are used.

Purification of α2M in complexed or non-complexed forms are described in the following subsections. Further, one skilled in the art can synthesize α2M by recombinant expression or peptide synthesis, which are also described below.

5.2.1. Preparation and Purification of Hsp70 or Hsp70-Peptide Complexes

The purification of noncovalently bound cellularly produced hsp70-peptide complexes has been described previously, see, for example, Udono et al., 1993, J. Exp. Med. 178:1391-1396. A procedure that may be used, presented by way of example but not limitation, is as follows:

Initially, human or mammalian cells are suspended in 3 volumes of 1× Lysis buffer consisting of 5 mM sodium phosphate buffer (pH 7), 150 mM NaCl, 2 mM $CaCl_2$, 2 mM $MgCl_2$, and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate (pH 7.5), 1 mM PMSF, incubated on ice for 20 minutes and then homogenized in a Dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose™ equilibrated with phosphate buffered saline (PBS) containing 2 mM $Ca^{2+}$ and 2 mM $Mg^{2+}$. When the cells are lysed by mechanical shearing the supernatant is diluted with an equal volume of 2× lysis buffer prior to mixing with Con A Sepharose™. The supernatant is then allowed to bind to the Con A Sepharose™ for 2-3 hours at 4° C. The material that fails to bind is harvested and dialyzed for 36 hours (three times, 100 volumes each time) against 10 mM Tris-Acetate (pH 7.5), 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC™ ion exchange chromatographic column (Pharmacia) equilibrated in 20 mM Tris-Acetate (pH 7.5), 20 mM NaCl, 0.1 mM EDTA and 15 mM 2-mercaptoethanol. The column is then developed with a 20 mM to 500 mM NaCl gradient and then eluted fractions fractionated by sodium dodecyl sulfate-polyacrylamide gel electrophoresis (SDS-PAGE) and characterized by immunoblotting using an appropriate anti-hsp70 antibody (such as from clone N27F3-4, from StressGen).

Fractions strongly immunoreactive with the anti-hsp70 antibody are pooled and the hsp70-peptide complexes precipitated with ammonium sulfate; specifically with a 50%-70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephade® G25 column (Pharmacia). If necessary the hsp70 preparation thus obtained can be repurified through the Mono Q FPLC™ ion exchange chromatographic column (Pharmacia) as described above.

The hsp70-peptide complex can be purified to apparent homogeneity using this method. Typically 1 mg of hsp70-peptide complex can be purified from 1 g of cells/tissue.

An improved method for purification of hsp70-peptide complexes comprises contacting cellular proteins with ADP or a nonhydrolyzable analog of ATP affixed to a solid substrate, such that hsp70 in the lysate can bind to the ADP or nonhydrolyzable ATP analog, and eluting the bound hsp70. A preferred method uses column chromatography with ADP affixed to a solid substratum (e.g., ADP-agarose). The resulting hsp70 preparations are higher in purity and devoid of contaminating peptides. The hsp70 complex yields are also increased significantly by about more than 10 fold. Alternatively, chromatography with nonhydrolyzable analogs of ATP, instead of ADP, can be used for purification of hsp70-peptide complexes. By way of example but not limitation, purification of hsp70-peptide complexes by ADP-agarose chromatography can be carried out as follows:

Meth A sarcoma cells (500 million cells) are homogenized in hypotonic buffer and the lysate is centrifuged at 100,000 g for 90 minutes at 4° C. The supernatant is applied to an ADP-agarose column. The column is washed in buffer and is eluted with 5 column volumes of 3 mM ADP. The hsp70-peptide complexes elute in fractions 2 through 10 of the total 15 fractions which elute. The eluted fractions are analyzed by SDS-PAGE. The hsp70-peptide complexes can be purified to apparent homogeneity using this procedure.

Separation of the HSP from an hsp70-peptide complex can be performed in the presence of ATP or low pH. These two methods may be used to elute the peptide from an hsp70-peptide complex. The first approach involves incubating an hsp70-peptide complex preparation in the presence of ATP. The other approach involves incubating an hsp70-peptide complex preparation in a low pH buffer. These methods and any others known in the art may be applied to separate the HSP and peptide from an hsp-peptide complex.

5.2.2. Preparation and Purification of Hsp90 or Noncovalent Cellularly Produced Hsp90-Peptide Complexes A procedure that can be used, presented by way of example and not limitation, is as follows:

Initially, human or mammalian cells are suspended in 3 volumes of IX Lysis buffer consisting of 5 mM sodium phosphate buffer (pH 7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate (pH 7.5), 1 mM PMSF, incubated on ice for 20 minutes and then homogenized in a Dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose™ equilibrated with PBS containing 2 mM $Ca^{2+}$ and 2 mM $Mg^{2+}$. When the cells are lysed by mechanical shearing the supernatant is diluted with an equal volume of 2× Lysis buffer prior to mixing with Con A Sepharose™. The supernatant is then allowed to bind to the Con A Sepharose™ for 2-3 hours at 4° C. The material that fails to bind is harvested and dialyzed for 36 hours (three times, 100 volumes each time) against 10 mM Tris-Acetate (pH 7.5), 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC™ ion exchange chromatographic column (Pharmacia) equilibrated with lysis buffer. The proteins are then eluted with a salt gradient of 200 mM to 600 mM NaCl.

The eluted fractions are fractionated by SDS-PAGE and fractions containing the hsp90-peptide complexes identified by immunoblotting using an anti-hsp90 antibody such as 3G3 (Affinity Bioreagents). Hsp90-peptide complexes can be purified to apparent homogeneity using this procedure. Typically, 150-200 μg of hsp90-peptide complex can be purified from 1 g of cells/tissue.

Separation of the HSP from an hsp90-peptide complex can be performed in the presence of ATP or low pH. These two methods may be used to elute the peptide from an hsp90-peptide complex. The first approach involves incubating an hsp90-peptide complex preparation in the presence of ATP. The other approach involves incubating an hsp90-peptide complex preparation in a low pH buffer. These methods and any others known in the art may be applied to separate the HSP and peptide from an hsp-peptide complex.

5.2.3. Preparation and Purification of Gp96 or Noncovalent Cellularly Produced Gp96-Peptide Complexes A procedure that can be used, presented by way of example and not limitation, is as follows:

A pellet of human or mammalian cells is resuspended in 3 volumes of buffer consisting of 30 mM sodium bicarbonate buffer (pH 7.5) and 1 mM PMSF and the cells allowed to swell on ice 20 minutes. The cell pellet is then homogenized in a Dounce homogenizer (the appropriate clearance of the homogenizer will vary according to each cell type) on ice until >95% cells are lysed.

The lysate is centrifuged at 1,000 g for 10 minutes to remove unbroken cells, nuclei and other debris. The supernatant from this centrifugation step is then recentrifuged at 100,000 g for 90 minutes. The gp96-peptide complex can be purified either from the 100,000 pellet or from the supernatant.

When purified from the supernatant, the supernatant is diluted with equal volume of 2× lysis buffer and the supernatant mixed for 2-3 hours at 4° C. with Con A Sepharose™ equilibrated with PBS containing 2 mM $Ca^{2+}$ and 2 mM $Mg^{2+}$. Then, the slurry is packed into a column and washed with 1× lysis buffer until the OD280, drops to baseline. Then, the column is washed with ⅓ column bed volume of 10% α-methyl mannoside (αMM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDSPAGE. Typically the resulting material is about 60-95% pure, however this depends upon the cell type and the tissue-to-lysis buffer ratio used. Then the sample is applied to a Mono Q FPLC™ ion exchange chromatographic column (Pharmacia) equilibrated with a buffer containing 5 mM sodium phosphate (pH 7). The proteins are then eluted from the column with a 0-1M NaCl gradient and the gp96 fraction elutes between 400 mM and 550 mM NaCl.

The procedure, however, may be modified by two additional steps, used either alone or in combination, to consistently produce apparently homogeneous gp96-peptide complexes. One optional step involves an ammonium sulfate precipitation prior to the Con A purification step and the other optional step involves DEAE-Sepharose™ purification after the Con A purification step but before the Mono Q FPLC™ step.

In the first optional step, described by way of example as follows, the supernatant resulting from the 100,000 g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A Sepharose™ and the procedure followed as before.

In the second optional step, described by way of example as follows, the gp96 containing fractions eluted from the Con A column are pooled and the buffer exchanged for 5 mM sodium phosphate buffer (pH 7), 300 mM NaCl by dialysis, or preferably by buffer exchange on a Sephadex G25 column. After buffer exchange, the solution is mixed with DEAE-Sepharose™ previously equilibrated with 5 mM sodium phosphate buffer (pH 7), 300 mM NaCl. The protein solution and the beads are mixed gently for 1 hour and poured into a column. Then, the column is washed with 5 mM sodium phosphate buffer (pH 7), 300 mM NaCl, until the absorbance at 280 nm drops to baseline. Then, the bound protein is eluted from the column with five volumes of 5 mM sodium phosphate buffer (pH 7), 700 mM NaCl. Protein containing fractions are pooled and diluted with 5 mM sodium phosphate buffer (pH 7) in order to lower the salt concentration to 175 mM. The resulting material then is applied to the Mono Q FPLC™ ion exchange chromatographic column (Pharmacia) equilibrated with 5 mM sodium phosphate buffer (pH 7) and the protein that binds to the Mono Q FPLC™ ion exchange chromatographic column (Pharmacia) is eluted as described before.

It is appreciated, however, that one skilled in the art may assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000 g pellet, the pellet is suspended in 5 volumes of PBS containing either 1% sodium deoxycholate or 1% oxtyl glucopyranoside (but without the $Mg^{2+}$ and $Ca^{2+}$) and incubated on ice for 1 hour. The suspension is centrifuged at 20,000 g for 30 minutes and the resulting supernatant dialyzed against several changes of PBS (also without the $Mg^{2+}$ and $Ca^{2+}$) to remove the detergent. The dialysate is centrifuged at 100,000 g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000 g supernatant, see above.

The gp96-peptide complexes can be purified to apparent homogeneity using this procedure. About 10-20 μg of gp96 can be isolated from 1 g cells/tissue.

Separation of the HSP from an gp96-peptide complex can be performed in the presence of ATP or low pH. These two methods may be used to elute the peptide from an gp96-peptide complex. The first approach involves incubating an gp96-peptide complex preparation in the presence of ATP. The other approach involves incubating an gp96-peptide complex preparation in a low pH buffer. These methods and any others known in the art may be applied to separate the HSP and peptide from an hsp-peptide complex.

5.2.4. Preparation and Purification of Noncovalent Cellularly Produced Hsp110-Peptide Complexes A procedure, described by Wang et al., 2001, J. Immunol. 166(1):490-7, that can be used, presented by way of example and not limitation, is as follows:

A pellet (40-60 ml) of cell or tissue, e.g., tumor cell tissue, is homogenized in 5 vol of hypotonic buffer (30 mN sodium bicarbonate, pH7.2, and protease inhibitors) by Dounce homogenization. The lysate is centrifuged at 4,500×g and then 100,000×g for 2 hours. If the cells or tissues are of hepatic origin, the resulting supernatant is first applied to a blue Sepharose column (Pharmacia) to remove albumin. Otherwise, the resulting supernatant is applied to a Con A-Sepharose column (Pharmacia Biotech, Piscataway, N.J.) previously equilibrated with binding buffer (20 mM Tris-HCl, pH 7.5; 100 mM NaCl; 1 mM $MgCl_2$; 1 mM $CaCl_2$; 1 mM $MnCl_2$; and 15 mM 2-ME), The bound proteins are eluted with binding buffer containing 15% α-D-o-methylmannoside (Sigma, St. Louis, Mo.).

Con A-Sepharose unbound material is first dialyzed against a solution of 20 mM Tris-HCl, pH 7.5; 100 mM NaCl; and 15 mM 2-ME, and then applied to a DEAE-Sepharose column and eluted by salt gradient from 100 to 500 mM NaCl. Fractions containing hsp110 are collected, dialyzed, and loaded onto a Mono Q (Pharmacia) 10/10 column equilibrated with 20 mM Tris-HCl, pH 7.5; 200 mM NaCl; and 15 mM 2-ME. The bound proteins are eluted with a 200-500 mM NaCl gradient. Fractions are analyzed by SDS-PAGE followed by immunoblotting with an Ab for hsp110, as described by Wang et al., 1999, J. Immunol, 162:3378. Pooled fractions containing hsp110 are concentrated by Centriplus (Amicon, Beverly, Mass.) and applied to a Superose 12 column (Pharmacia). Proteins are eluted by 40 mM Tris-HCl, pH 8.0; 150 mM NaCl; and 15 mM 2-ME with a flow rate of 0.2 ml/min.

5.2.5. Preparation and Purification of Noncovalent Cellularly Produced Grp170-Peptide Complexes A procedure, described by Wang et al., 2001, J. Immunol. 166(1):490-7, that can be used, presented by way of example and not limitation, is as follows:

A pellet (40-60 ml) of cell or tissue, e.g., tumor cell tissue, is homogenized in 5 vol of hypotonic buffer (30 mN sodium bicarbonate, pH7.2, and protease inhibitors) by Dounce homogenization. The lysate is centrifuged at 4,500×g and then 100,000×g for 2 hours. If the cells or tissues are of hepatic origin, the resulting supernatant is first applied to a blue Sepharose column (Pharmacia) to remove albumin. Otherwise, the resulting supernatant is applied to a Con A-Sepharose column (Pharmacia Biotech, Piscataway, N.J.) previously equilibrated with binding buffer (20 mM Tris-HCl, pH 7.5; 100 mM NaCl; 1 mM $MgCl_2$; 1 mM $CaCl_2$; 1 mM $MnCl_2$; and 15 mM 2-ME). The bound proteins are eluted with binding buffer containing 15% α-D-o-methylmannoside (Sigma, St. Louis, Mo.).

Con A-Sepharose-bound material is first dialyzed against 20 mM Tris-HCl, pH 7.5, and 150 mind NaCl and then applied to a Mono Q column and eluted by a 150 to 400 mM NaCl gradient. Pooled fractions are concentrated and applied on the Superose 12 column (Pharmacia). Fractions containing homogeneous grp170 are collected.

5.2.6. α2M-Antigenic Molecule Complexes

Endogenous α2M-antigenic molecule complexes can be obtained by the following non-limiting methods.

Alpha-2-macroglobulin can be bought from commercial sources or prepared by purifying it from human blood. To purify α2M from blood, the following non-limiting protocol can be used:

Blood is collected from a subject and is allowed to clot. It is then centrifuged for 30 minutes under 14,000×g to obtain the serum which is then applied to a gel filtration column (Sephacryl S-300R) equilibrated with 0.04M Tris buffer pH 7.6 plus 0.3M NaCl. A 65 ml column is used for about 10 ml of serum. Three ml fractions are collected and each fraction is tested for the presence of α2M by dot blot using an α2M specific antibody. The α2M positive fractions are pooled and applied to a PD10 column to exchange the buffer to 0.01M Sodium Phosphate buffer pH 7.5 with PMSF. The pooled fractions are then applied to a Con A column (10 ml) equilibrated with the phosphate buffer. The column is washed and the protein is eluted with 5% methylmannose pyranoside. The eluent is passed over a PD10 column to change the buffer to a Sodium Acetate buffer (0.05M; pH6.0). A DEAE column is then equilibrated with acetate buffer and the sample is applied to the DEAE column. The column is washed and the protein is eluted with 0.13M sodium acetate. The fractions with α2M are then pooled.

5.2.7. Recombinant Expression of HSPs and α2M and Antigenic Peptides

Methods known in the art can be utilized to recombinantly produce HSPs and α2M. A nucleic acid sequence encoding a heat shock protein or encoding α2M can be inserted into an expression vector for propagation and expression in host cells.

An expression construct, as used herein, refers to a nucleotide sequence encoding an HSP or α2M operably associated with one or more regulatory regions which enables expression of the HSP or α2M in an appropriate host cell. "Operably-associated" refers to an association in which the regulatory regions and the HSP or α2M sequence to be expressed are joined and positioned in such a way as to permit transcription, and ultimately, translation.

The regulatory regions necessary for transcription of the HSP or α2M can be provided by the expression vector. A translation initiation codon (ATG) may also be provided if the HSP or α2M gene sequence lacking its cognate initiation codon is to be expressed. In a compatible host-construct system, cellular transcriptional factors, such as RNA polymerase, will bind to the regulatory regions on the expression construct to effect transcription of the modified HSP or α2M sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to the HSP or α2M gene sequence or to insert the HSP or α2M gene sequence into the cloning site of a vector, linkers or adapters providing the appropriate compatible restriction sites may be ligated to the ends of the cDNAs by techniques well known in the art (Wu et al., 1987, Methods in Enzymol 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising an HSP or α2M sequence operably associated with regulatory regions can be directly introduced into appropriate host cells for expression and production of HSP-peptide complexes and α2M-peptide complexes without further cloning. See, for example, U.S. Pat. No. 5,580,859. The expression constructs can also contain DNA sequences that facilitate integration of the HSP or α2M sequence into the genome of the host cell, e.g., via homologous recombination. In this instance, it is not necessary to employ an expression vector comprising a replication origin suitable for appropriate host cells in order to propagate and express the HSP or α2M in the host cells.

A variety of expression vectors may be used including, but not limited to, plasmids, cosmids, phage, phagemids or modified viruses. Typically, such expression vectors comprise a functional origin of replication for propagation of the vector in an appropriate host cell, one or more restriction endonuclease sites for insertion of the HSP or α2M gene sequence, and one or more selection markers. The expression vector must be used with a compatible host cell which may be derived from a prokaryotic or an eukaryotic organism including but not limited to bacteria, yeasts, insects, mammals and humans.

For long term, high yield production of properly processed HSP/α2M or HSP-peptide/α2M-peptide complexes, stable expression in mammalian cells is preferred. Cell lines that stably express HSP/α2M or HSP-peptide/α2M-peptide complexes may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while HSP/α2M is expressed continuously.

The recombinant cells may be cultured under standard conditions of temperature, incubation time, optical density and media composition. However, conditions for growth of recombinant cells may be different from those for expression of HSPs/α2M and antigenic proteins. Modified culture conditions and media may also be used to enhance production of the HSP/α2M. For example, recombinant cells containing HSPs with their cognate promoters may be exposed to heat or other environmental stress, or chemical stress. Any techniques known in the art may be applied to establish the optimal conditions for producing HSP/α2M or HSP-peptide/α2M-peptide complexes.

Cells may be derived from a variety of sources, including, but not limited to, cells infected with an infectious agent and cancer cells and include, but are not limited to, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. The choice of cell type depends on the type of tumor or infectious disease being treated or prevented, and can be determined by one of skill in the art. In a specific embodiment, an expression construct comprising a nucleic acid sequence encoding the HSP/α2M polypeptide is introduced into an antigenic cell. As used herein, antigenic cells may include cells that are infected with an infectious agent or pathogen, cells infected with non-infectious or non-pathogenic forms of an infectious agent or pathogen (e.g., by use of a helper infectious agent), cells infected by or engineered to express an attenuated form of an infectious agent or a non-pathogenic or replication-deficient variant of a pathogen, pre-neoplastic cells that are infected with a cancer-causing infectious agent, such as a virus, but which are not yet neoplastic; or antigenic cells that have been exposed to a mutagen or cancer-causing agent, such as, for example DNA-damaging agents, radiation, etc. Other cells that can be used are pre-neoplastic cells which are in transition from a normal to a neoplastic form as characterized by morphology, physiological or biochemical functions. Preferably, the cancer cells and pre-neoplastic cells used in the methods of the invention are of mammalian origin. Mammals contemplated by this aspect of the invention include humans, companion animals (e.g., dogs and cats), livestock animals (e.g., sheep, cattle, goats, pigs and horses), laboratory animals (e.g., mice, rats and rabbits), and captive or free wild animals.

In various embodiments, any cancer cell, preferably a human cancer cell, can be used in the present methods for producing the peptide-complexes. The cancer cells provide the antigenic peptides which become associated covalently or noncovalently with the expressed HSP/α2M polypeptide. The peptide-complexes are then purified from the cells and used to treat such cancers. Cancers which can be treated or prevented with immunogenic compositions prepared by methods of the invention include, but are not limited to, tumors such as sarcomas and carcinomas. Accordingly, any tissues or cells isolated from a pre-neoplastic lesion, a cancer, including cancer that has metastasized to multiple remote sites, can be used in the present method. For example, cells found in abnormally growing tissue, circulating leukemic cells, metastatic lesions as well as solid tumor tissue can be used.

In another embodiment, cell lines derived from a pre-neoplastic lesion, cancer tissues or cancer cells can also be used, provided that the cells of the cell line have at least one or more antigenic determinants in common with antigens on the target cancer cells. Cancer tissues, cancer cells, cells infected with a cancer-causing agent, other pre-neoplastic cells, and cell lines of human origin are preferred.

Cancer and pre-neoplastic cells can be identified by any method known in the art. For example, cancer cells can be identified by morphology, enzyme assays, proliferation assays, cytogenetic characterization, DNA mapping, DNA sequencing, the presence of cancer-causing virus, or a history of exposure to mutagen or cancer-causing agent, imaging, etc. Cancer cells may also be obtained by surgery, endoscopy, or other biopsy techniques. If some distinctive characteristics of the cancer cells are known, they can also be obtained or purified by any biochemical or immunological methods known in the art, such as but not limited to affinity chromatography, and fluorescence activated cell sorting (e.g., with fluorescently tagged antibody against an antigen expressed by the cancer cells).

Cancer tissues, cancer cells or cell lines may be obtained from a single individual or pooled from several individuals. It is not essential that clonal, homogeneous, or purified population of cancer cells be used. It is also not necessary to use cells of the ultimate target in vivo (e.g., cells from the tumor of the intended recipient), so long as at least one or more antigenic determinants on the target cancer cells is present on the cells used for expression of the HSP/α2M polypeptide. In addition, cells derived from distant metastases may be used to prepare an immunogenic composition against the primary cancer. A mixture of cells can be used provided that a substantial number of cells in the mixture are cancer cells and share at least one antigenic determinant with the target cancer cell. In a specific embodiment, the cancer cells to be used in expressing an HSP/α2M polypeptide are purified.

5.2.8. Peptide Synthesis

An alternative to producing HSP/α2M by recombinant techniques is peptide synthesis. For example, an entire HSP/α2M, or a peptide corresponding to a portion of an HSP/α2M can be synthesized by use of a peptide synthesizer. Conventional peptide synthesis or other synthetic protocols well known in the art may be used.

Peptides having the amino acid sequence of an HSP/α2M or a portion thereof may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting HSP/α2M is accomplished using conventional procedures, such as preparative HPLC using gel permeation, partition and/or ion exchange chromatography. The choice of appropriate matrices and buffers are well known in the art and so are not described in detail herein.

5.3 Antigenic Molecules

The following subsections provide an overview of peptides that are useful as antigenic/immunogenic components of the HSP/α2M-peptide complexes of the invention, and how such peptides can be identified, e.g., for use in recombinant expression of the peptides for in vitro complexing of HSPs/α2M and antigenic molecules. However, in the practice of the present invention, the identity of the antigenic molecule(s) of the HSP/α2M peptide-complex need not be known, for example when the HSP/α2M complex is purified directly from a cancerous cell or from a tissue infected with a pathogen.

5.3.1. Isolation of Antigenic/Immunogenic Components

It has been found that antigenic peptides and/or components can be eluted from HSP/α2M complexes either in the presence of ATP or low pH. These experimental conditions may be used to isolate peptides and/or antigenic components from cells which may contain potentially useful antigenic determinants. Once isolated, the amino acid sequence of each antigenic peptide may be determined using conventional amino acid sequencing methodologies.

Such antigenic molecules can then be produced by chemical synthesis or recombinant methods, purified, and complexed to HSPs in vitro to form the HSP complexes of the invention.

Similarly, it has been found that potentially immunogenic peptides may be eluted from MHC-peptide complexes using techniques well known in the art (Falk, K. et al., 1990 Nature 348:248-251; Elliott, T., et al., 1990, Nature 348:195-197; Falk, K., et al., 1991, Nature 351:290-296).

Thus, potentially immunogenic or antigenic peptides may be isolated from either endogenous stress protein-peptide complexes or endogenous MHC-peptide complexes for use subsequently as antigenic molecules, by complexing in vitro to HSP/α2M to form the HSP/α2M complexes of the invention. Exemplary protocols for isolating peptides and/or antigenic components from either of these complexes are known in the art are described hereinbelow.

5.3.2. Peptides from Stress Protein-Peptide Complexes

Two methods may be used to elute the peptide from a stress protein-peptide complex.

One approach involves incubating the stress protein-peptide complex in the presence of ATP. The other approach involves incubating the complexes in a low pH buffer.

Briefly, the complex of interest is centrifuged through a Centricon 10 assembly (Millipore) to remove any low molecular weight material loosely associated with the complex. The large molecular weight fraction may be removed and analyzed by SDS-PAGE while the low molecular weight may be analyzed by HPLC as described below. In the ATP incubation protocol, the stress protein-peptide complex in the large molecular weight fraction is incubated with 10 mM ATP for 30 minutes at room temperature. In the low pH protocol, acetic acid or trifluoroacetic acid (TFA) is added to the stress protein-peptide complex to give a final concentration of 10%

(vol/vol) and the mixture incubated at room temperature or in a boiling water bath or any temperature in between, for 10 minutes (See, Van Bleek, et al., 1990, Nature 348:213-216; and Li, et al., 1993, EMBO Journal 12:3143-3151).

The resulting samples are centrifuged through a Centricon 10 assembly as mentioned previously. The high and low molecular weight fractions are recovered. The remaining large molecular weight stress protein-peptide complexes can be reincubated with ATP or low pH to remove any remaining peptides.

The resulting lower molecular weight fractions are pooled, concentrated by evaporation and dissolved in 0.1% TFA. The dissolved material is then fractionated by reverse phase high pressure liquid chromatography (HPLC) using for example a VYDAC C18 reverse phase column equilibrated with 0.1% TFA. The bound material is then eluted at a flow rate of about 0.8 ml/min by developing the column with a linear gradient of 0 to 80% acetonitrile in 0.1% TFA. The elution of the peptides can be monitored by OD210 and the fractions containing the peptides collected.

5.3.3. Peptides from MHC-Peptide Complexes

The isolation of potentially immunogenic peptides from MHC molecules is well known in the art and so is not described in detail herein (See, Falk, et al., 1990, Nature 348:248-251; Rotzsche, et al., 1990, Nature 348:252-254; Elliott, et al., 1990, Nature 348:191-197; Falk, et al., 1991, Nature 351:290-296; Demotz, et al., 1989, Nature 343:682-684; Rotzsche, et al., 1990, Science 249:283-287), the disclosures of which are incorporated herein by reference.

Briefly, MHC-peptide complexes may be isolated by a conventional immunoaffinity procedure. The peptides then may be eluted from the MHC-peptide complex by incubating the complexes in the presence of about 0.1% TFA in acetonitrile. The eluted peptides may be fractionated and purified by reverse phase HPLC, as before.

The amino acid sequences of the eluted peptides may be determined either by manual or automated amino acid sequencing techniques well known in the art. Once the amino acid sequence of a potentially protective peptide has been determined the peptide may be synthesized in any desired amount using conventional peptide synthesis or other protocols well known in the art.

Peptides having the same amino acid sequence as those isolated above may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile.

Briefly, the C-terminal N-α-protected amino acid is first attached to the polystyrene beads, The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting peptides is accomplished using conventional procedures, such as preparative HPLC using gel permeation, partition and/or ion exchange chromatography. The choice of appropriate matrices and buffers are well known in the art and so are not described in detail herein.

5.3.4. Exogenous Antigenic Molecules

Molecules that display the antigenicity of a known antigen of a pathogen or of a tumor-specific or tumor-associated antigen of a cancer type, e.g. antigens or antigenic portions thereof, can be selected for use as antigenic molecules, for complexing to HSP/α2M, from among those known in the art or determined by immunoassay to be able to bind to antibody or MHC molecules (antigenicity) or generate immune response (immunogenicity). To determine immunogenicity or antigenicity by detecting binding to antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are envisioned for use. In one embodiment for detecting immunogenicity, T cell-mediated responses can be assayed by standard methods, e.g., in vitro cytoxicity assays or in vivo delayed-type hypersensitivity assays.

Potentially useful antigens or derivatives thereof for use as antigenic molecules can also be identified by various criteria, such as the antigen's involvement in neutralization of a pathogen's infectivity (wherein it is desired to treat or prevent infection by such a pathogen) (Norrby, 1985, Summary, in Vaccines 85, Lerner, et al. (eds.), Cold Spring Harbor Laboratory, Cold Spring Harbor, N.Y., pp. 388-389), type or group specificity, recognition by patients' antisera or immune cells, and/or the demonstration of protective effects of antisera or immune cells specific for the antigen. In addition, where it is desired to treat or prevent a disease caused by pathogen, the antigen's encoded epitope should preferably display a small or no degree of antigenic variation in time or amongst different isolates of the same pathogen.

Preferably, where it is desired to treat or prevent cancer, known tumor-specific (i.e., expressed in tumor cells) or tumor associated antigens (i.e., relatively overexpressed in tumor cells) or fragments or derivatives thereof are used. For example, such tumor specific or tumor-associated antigens include but are not limited to KS 1/4 pan-carcinoma antigen (Perez and Walker, 1990, J. Immunol. 142:3662-3667;

Bumal, 1988, Hybridoma 7(4):407-415); ovarian carcinoma antigen (CA125) (Yu, et al., 1991, Cancer Res. 51(2):468-475); prostatic acid phosphate (Tailer, et al., 1990, Nucl. Acids Res. 18(16):4928); prostate specific antigen (Henttu and Vihko, 1989, Biochem. Biophys. Res. Comm. 160(2): 903-910; Israeli, et al., 1993, Cancer Res. 53:227-230); melanoma-associated antigen p97 (Estin, et al., 1989, J. Natl. Cancer Inst. 81(6):445-446); melanoma antigen gp75 (Vijayasardahl, et al., 1990, J. Exp. Med. 171(4):1375-1380); high molecular weight melanoma antigen (Natali, et al., 1987, Cancer 59:55-63) and prostate specific membrane antigen. Other exogenous antigens that may be complexed to HSPs/α2M include portions or proteins that are mutated at a high frequency in cancer cells, such as oncogenes (e.g., ras, in particular mutants of ras with activating mutations, which only occur in four amino acid residues (12, 13, 59 or 61) (Gedde-Dahl et al., 1994, Eur. J. Immunol. 24(2):410-414)) and tumor suppressor genes (e.g., p53, for which a variety of mutant or polymorphic p53 peptide antigens capable of stimulating a cytotoxic T cell response have been identified (Gnjatic et al., 1995, Eur. J. Immunol. 25(6):1638-1642).

In a specific embodiment, an antigen or fragment or derivative thereof specific to a certain tumor is selected for complexing to HSPs/α2M to form an HSP/α2M complex for administration to a patient having that tumor.

Preferably, where it is desired to treat or prevent viral diseases, molecules comprising epitopes of known viruses are used. For example, such antigenic epitopes may be prepared from viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II). Preferably, where it is desired to treat or prevent bacterial infections, molecules comprising epitopes of known bacteria are used. For example, such antigenic epitopes may be prepared from bacteria including, but not limited to, mycobacteria *rickettsia, mycoplasma, neisseria* and *legionella*.

Preferably, where it is desired to treat or prevent protozoal infections, molecules comprising epitopes of known protozoa are used. For example, such antigenic epitopes may be prepared from protozoa including, but not limited to, *leishmania, kokzidioa*, and *trypanosoma*.

Preferably, where it is desired to treat or prevent parasitic infections, molecules comprising epitopes of known parasites are used. For example, such antigenic epitopes may be from parasites including, but not limited to, *chlamydia* and *rickettsia*.

5.4. In Vitro Production of Non-Covalent HSP/α2M Complexes

In an embodiment in which HSPs/α2M and the peptides with which they are endogenously associated in vivo are not employed, complexes of HSPs/α2M to antigenic molecules are produced in vitro. As will be appreciated by those skilled in the art, the peptides either isolated by the aforementioned procedures or chemically synthesized or recombinantly produced may be reconstituted with a variety of purified natural or recombinant stress proteins in vitro to generate immunogenic non-covalent stress protein-antigenic molecule complexes. Alternatively, exogenous antigens or antigenic or immunogenic fragments or derivatives thereof can be complexed to stress proteins. A preferred, exemplary protocol for complexing a stress protein and an antigenic molecule in vitro is discussed below.

In a method which produces non-covalent HSP-antigenic molecule complexes and α2M-antigenic molecule complexes, a complex is prepared according to the method described by Blachere et al., 1997 J. Exp. Med. 186(8):1315-22, which incorporated by reference herein in its entirety. Blachere teaches in vitro complexing of hsps to antigenic molecule. The protocol described in Blachere can be modified such that the hsp component is substituted by α2M. Binder et al. (2001, J. Immunol. 166:4968-72) demonstrates that the Blachere method yields complexes of α2M bound to antigenic molecules.

Prior to complexing, the HSPs/α2M are pretreated with ATP or low pH to remove any peptides that may be associated with the HSP/α2M of interest. When the ATP procedure is used, excess ATP is removed from the preparation by the addition of apyranase as described by Levy, et al., 1991, Cell 67:265-274. When the low pH procedure is used, the buffer is readjusted to neutral pH by the addition of pH modifying reagents.

The antigenic molecules and the pretreated HSP/α2M are admixed to give an approximately 5 antigenic molecule: 1 stress protein molar ratio. Then, the mixture is incubated for 15 minutes to 3 hours at 4° to 45° C. in a suitable binding buffer such as one containing 20 mM sodium phosphate, pH 7.2, 350 mM NaCl, 3 mM MgCl2 and 1 mM phenyl methyl sulfonyl fluoride (PMSF). The preparations are centrifuged through a Centricon 10 assembly (Millipore) to remove any unbound peptide. The association of the peptides with the stress proteins can be assayed by SDS-PAGE. This is the preferred method for in vitro complexing of peptides isolated from MHC-peptide complexes of peptides disassociated from endogenous HSP peptide complexes.

In an alternative embodiment of the invention, preferred for producing complexes of hsp70 to exogenous antigenic molecules such as proteins, 5-10 micrograms of purified HSP is incubated with equimolar quantities of the antigenic molecule in 20 mM sodium phosphate buffer pH 7.5, 0.5M NaCl, 3 mM $MgCl_2$ and 1 mM ADP in a volume of 100 microliter at 37° C. for 1 hr. This incubation mixture is further diluted to 1 ml in phosphate-buffered saline.

In an alternative embodiment of the invention, preferred for producing complexes of gp96 or hsp90 to peptides, 5-10 micrograms of purified gp96 or hsp90 is incubated with equimolar or excess quantities of the antigenic peptide in a suitable buffer such as one containing 20 mM sodium phosphate buffer pH 7.5, 0.5M NaCl, 3 nM $MgCl_2$ at 60-65° C. for 5-20 min. This incubation mixture is allowed to cool to room temperature and centrifuged one or more times if necessary, through a Centricon 10 assembly (Millipore) to remove any unbound peptide.

Antigenic molecules may be isolated from various sources, chemically synthesized, or produced recombinantly. Such methods can be readily adapted for medium or large scale production of the immunotherapeutic or prophylactic vaccines.

Following complexing, the immunogenic antigenic molecule complexes can optionally be assayed in vitro using, for example, the mixed lymphocyte target cell assay (MLTC) described below. Once immunogenic complexes have been isolated they can be optionally characterized further in animal models using the preferred administration protocols and excipients discussed below.

5.5. Formation of Covalent HSP/α2M Complexes

As an alternative to non-covalent complexes of HSPs/α2M and antigenic molecules, antigenic molecules may be covalently attached to HSPs/α2M. HSP/α2M peptide complexes are preferably cross-linked after their purification from cells or tissues. Covalently linked complexes are the complexes of choice when a B cell response is desired.

In one embodiment, HSPs/α2M are covalently coupled to antigenic molecules by chemical crosslinking. Chemical crosslinking methods are well known in the art. For example, in a preferred embodiment, glutaraldehyde crosslinking may be used. Glutaradehyde crosslinking has been used for formation of covalent complexes of peptides and hsps (see Barrios et al., 1992, Eur. J. Immunol. 22: 1365-1372). Preferably, 1-2 mg of HSP peptide complex is crosslinked in the presence of 0.002% glutaraldehyde for 2 hours. Glutaraldehyde is removed by dialysis against phosphate buffered saline (PBS) overnight (Lussow et al., 1991, Eur. J. Immunol. 21: 2297-2302). In one embodiment, the following protocol is used. Optionally, HSPs may be pretreated with ATP or low pH prior to complexing, in order to remove any peptides that may be associated with the HSP polypeptide. Preferably, 1 mg of HSP is crosslinked to 1 mg of peptide in the presence of 0.002% glutaraldehyde for 2 hours. Glutaraldehyde is removed by dialysis against phosphate buffered saline (PBS) overnight (Lussow et al., 1991, Eur. J. Immunol. 21: 2297-2302).

Other methods for chemical crosslinking may also be used, in addition other methods for covalent attachment of proteins, such as photocrosslinking (see Current Protocols in Molecular Biology, Ausubel et al. (eds.), Greene Publishing Associates and Wiley Interscience, New York).

In another embodiment, the HSP and specific antigen(s) are crosslinked by ultraviolet (UV) crosslinking.

In one embodiment, HSPs are covalently coupled to peptide fragments by chemical crosslinking. Chemical crosslinking methods are well known in the art. For example, in a preferred embodiment, glutaraldehyde crosslinking may be used. Glutaradehyde crosslinking has been used for formation of covalent complexes of peptides and HSPs (see Barrios et al., 1992, Eur. J. Immunol. 22: 1365-1372). Preferably, 1-2 mg of HSP-peptide complex is crosslinked in the presence of 0.002% glutaraldehyde for 2 hours. Glutaraldehyde is removed by dialysis against phosphate buffered saline (PBS) overnight (Lussow et al., 1991, Eur. J. Immunol. 21: 2297-2302). Alternatively, an HSP and a population of peptides can be crosslinked by ultraviolet (UV) crosslinking under conditions known in the art.

In another embodiment of the invention, a population of peptides can be complexed to α2M by incubating the peptide fragments with α2M at a 50:1 molar ratio and incubated at 50° C. for 10 minutes followed by a 30 minute incubation at 25° C. Free (uncomplexed) peptides are then removed by size exclusion filters. Protein-peptide complexes are preferably measured by a scintillation counter to make sure that on a per molar basis, each protein is observed to bind equivalent amounts of peptide (approximately 0.1% of the starting amount of the peptide). For details, see Binder, 2001, J. Immunol. 166(8):4968-72, which is incorporated herein by reference in its entirety.

Alternatively, a population of antigenic peptides can be complexed to α2M covalently by methods as described in PCT publications WO 94/14976 and WO 99/50303 for complexing a peptide to α2M, which are incorporated herein by reference in their entirety. Covalent linking of a population of antigenic peptides to α2M can be performed using a bifunctional crosslinking agent. Such crosslinking agents and methods of their use are also well known in the art.

In general, when an α2M is mixed with a protease, cleavage of the "bait" region of α2M takes place, the proteinase becomes "trapped" by thioesters, and a conformational change takes place that allows binding of the α2M complex to the α2M receptor. During proteolytic activation of α2M, non-proteolytic ligands can become covalently bound to the activated thioesters. Non-proteolytic ligands can also be incorporated into the activated α2M molecule by ammonia or methylamine during reversal of the nucleophilic activation, employing heat (Grøn and Pizzo, 1998, Biochemistry, 37: 6009-6014). Such conditions that allow fortuitous trapping of peptides by α2M are employed to prepare the α2M-antigenic complexes for use in the invention. Methods for such covalent coupling have been described previously (Osada et al., 1987, Biochem. Biophys. Res. Commun. 146:26-31; Osada et al., 1988, Biochem. Biophys. Res. Commun. 150:883; Chu and Pizzo, 1993, J. Immunol. 150:48; Chu et al., 1994, Ann. N.Y. Acad. Sci. 737:291-307; Mitsuda et al., 1993, Biochem. Biophys. Res. Commun. 101:1326-1331). Thus in one embodiment, an α2M antigenic molecule complex can be prepared as described by Grøn and Pizzo, 1998, Biochemistry, 37: 6009-6014. The method of Grøn and Pizzo yields complexes of α2M that are covalently bound to antigenic molecules.

For example, α2M polypeptide is mixed with an antigenic molecule in the presence of a protease, ammonia or other small amine nucleophiles such as methylamine and ethylamine. Non-limiting examples of proteases which may be used include trypsin, porcine pancreatic elastase (PEP), human neutrophil elastase, cathepsin G, S. aureus V-8 proteinase trypsin, α-chymotrypsin, V8 protease, papain, and proteinase K (see Ausubel et al., eds., in "Current Protocols in Molecular Biology", Greene Publishing Associates and Wiley Interscience, New York, 17.4.6-17.4.8). A preferred, exemplary protocol for complexing an α2M polypeptide and an antigenic molecule in vitro follows. The antigenic molecules (1 μg-20 mg) and the α2M polypeptide (1 μg-20 mg) are mixed together in phosphate-buffered saline (PBS) (100 μl-5 ml) in the presence of a protease, such as trypsin (0.92 mg trypsin in approximately 500 μl PBS, to give an approximately 5:1 antigenic molecule: α2M polypeptide molar ratio. The mixture is then incubated for 5-15 minutes at 37° C. 500 μl 4 mg/ml p-Aphenyl methyl sulfonyl fluoride (p-APMSF) is added to the solution to inhibit trypsin activity and incubated for 2 hrs at 25° C. The preparations can be centrifuged through a Centricon 10 assembly (Millipore) to remove any unbound peptide. Alternatively, free antigenic molecule may be removed by passage over a gel permeation column. The association of the peptides with the α2M polypeptide can be assayed by SDS-PAGE. This is the preferred method for in vitro complexing of antigenic molecules isolated from MHC-antigenic molecule complexes, or peptides disassociated from endogenous α2M-antigenic molecule complexes. The foregoing methods could readily be used to generate HSP-peptide complexes.

5.6. HSP or α2M Fusion Proteins

In certain embodiments of the invention, an HSP/α2M antigenic molecule complex is a recombinant fusion protein. Such recombinant fusion proteins, comprised of HSP/α2M sequences linked to antigenic molecule sequences, may be used in the methods of the present invention. To produce such a recombinant fusion protein, an expression vector is constructed using nucleic acid sequences encoding the HSP/α2M fused to sequences encoding an antigenic molecule, using recombinant methods known in the art (see Suzue et al., 1997, Proc. Natl. Acad. Sci. U.S.A. 94: 13146-51). HSP/α2M antigenic peptide fusions are then expressed and isolated. By specifically designing the antigenic peptide portion of the molecule, such fusion proteins can be used to elicit an immune response and in immunotherapy against target cancer and infectious diseases.

5.7. Kits, Dosage Regimens, Administration and Formulations

Kits are also provided for carrying out the therapeutic methods of the present invention. In one embodiment, a kit comprises a first container containing a purified HSP preparation or α2M preparation and a second container containing a non-vaccine therapeutic modality for treatment of cancer. Preferably, the cancer is CML, the HSP preparation comprises hsp70-peptide complexes, and the therapeutic modality is Gleevec™. In a specific embodiment, the second container contains imatinib mesylate. In another specific embodiment, the imatinib mesylate is purified. In a specific embodiment, a kit comprises a first container containing a purified HSP preparation or α2M preparation in an amount ineffective to treat a disease or disorder when administered alone; and a second container containing a non-vaccine treatment modality in an amount that, when administered before, concurrently with, or after the administration of the HSP preparation or α2M preparation in the first container, is effective to improve overall treatment effectiveness over the effectiveness of the administration of each component alone. In another specific embodiment, a kit comprises a first container containing a purified HSP preparation or α2M preparation in an amount ineffective to treat a disease or disorder when administered alone; and a second container containing one or more non-vaccine treatment modalities in an amount that, when administered before, concurrently with, or after the administration of the HSP preparation or α2M preparation in the first container, is effective to improve overall treatment effectiveness over the effectiveness of the administration of the HSP preparation or α2M preparation administered alone or the treatment modalities administered alone. In yet another specific embodiment, a first container containing a purified HSP preparation or α2M preparation in an amount ineffective to treat a disease or disorder when administered alone; and a second container and third container, each containing a non-vaccine treatment modality in an amount that, when administered before, concurrently with, or after the administration of the HSP preparation or α2M preparation in the first container, is effective to improve overall treatment effectiveness over the effectiveness of the administration of HSP preparation or α2M preparation administered alone or treatment modalities administered alone. In a preferred specific embodiment, the invention provides a kit comprising in a first container, a purified HSP preparation or α2M comprising a population of noncovalent HSP-peptide complexes α2M-peptide complexes obtained from cancerous tissue of a mammal; in a second container, a composition comprising a purified cancer chemotherapeutic agent; and in a third container, a composition comprising a purified cytokine. In a specific embodiment, the second container containing imatinib mesylate contains purified imatinib mesylate.

The dosage of HSP preparation or α2M preparation to be administered depends to a large extent on the condition and size of the subject being treated as well as the amount of non-vaccine treatment modality administered, the frequency of treatment and the route of administration. Regimens for continuing therapy, including site, dose and frequency may be guided by the initial response and clinical judgment.

Depending on the route of administration and the type of HSPs in the HSP preparation, the amount of HSP in the HSP preparation can range, for example, from 0.1 to 1000 μg per administration. The preferred amounts of gp96 or hsp70 are in the range of 10 to 600 μg per administration and 0.1 to 100 μg if the HSP preparation is administered intradermally. A particularly preferred amount of hsp70 is about 50 μg per administration if administered intradermally. For hsp 90, the preferred amounts are about 50 to 1000 μg per administration, and about 5 to 50 μg for intradermal administration. The amount of α2M administered can range from 2 to 1000 μg, preferably 20 to 500 μg, most preferably about 25 to 250 μg, given once weekly for about 4-6 weeks, intradermally with the site of administration varied sequentially.

Because in certain embodiments, the methods of the invention use administration of HSP preparation in sub-optimal amounts, it is envisioned that depending on the route of administration and the type of HSPs in the HSP preparation, the amount of HSP in the HSP preparation can be less than an amount in the range of 0.1 to 1000 μg per administration. Accordingly, the preferred amounts of gp96 or hsp70 are in amounts less than the range of 10 to 600 μg per administration and less than the range of 0.1 to 10 μg if the HSP preparation is administered intradermally. For hsp 90, the preferred amounts are less than the range of 50 to 1000 μg per administration, and less than the range of 5 to 50 μg for intradermal administration. The amount of α2M administered can range from less than the range of 2 to 1000 μg, preferably less than the range of 20 to 500 μg, most preferably less than the range of 25 to 250 μg, given once weekly for about 4-6 weeks, intradermally with the site of administration varied sequentially.

Solubility and the site of the administration of the treatment modality are factors which should be considered when choosing the route of administration of the HSP preparation of the invention. The mode of administration can be varied, including, but not limited to, e.g., subcutaneously, intravenously, intraperitoneally, intramuscularly, intradermally or mucosally. Mucosal routes can further take the form of oral, rectal and nasal administration. With the above factors taken into account, it may be preferable to administer the HSP to a site that is the same or proximal to the site of administration of the treatment modality.

In an embodiment of the invention, HSPs/α2M may be administered using any desired route of administration. Advantages of intradermal administration include use of lower doses and rapid absorption, respectively. Advantages of subcutaneous or intramuscular administration include suitability for some insoluble suspensions and oily suspensions, respectively. Mucosal routes of administration include, but are not limited to, oral, rectal and nasal administration. Preparations for mucosal administrations are suitable in various formulations as described below.

If the HSP/α2M preparation is water-soluble, then it may be formulated in an appropriate buffer, for example, phosphate buffered saline or other physiologically compatible solutions, preferably sterile. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, or rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such a liquid preparation may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical preparation may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

The HSP/α2M preparation for oral administration may be suitably formulated to give controlled release of the active compound.

For buccal administration, the preparation may take the form of tablets or lozenges formulated in conventional manner.

The preparation may be formulated for parenteral administration by injection, e.g., by bolus injection or continuous infusion. Formulations for injection may be presented in unit dosage form, e.g., in ampoules or in multi-dose containers, with an added preservative. The preparation may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The preparation may also be formulated in a rectal preparation such as a suppository or retention enema, e.g., containing conventional suppository bases such as cocoa butter or other glycerides.

In addition to the formulations described previously, the preparation may also be formulated as a depot preparation. Such long acting formulations may be administered by implantation (for example, subcutaneously or intramuscularly) or by intramuscular injection. Thus, for example, the preparation may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

For administration by inhalation, the preparation for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The preparation may, if desired, be presented in a pack or dispenser device which may contain one or more unit dosage forms containing the HSP preparation or α2M preparation. The pack may for example comprise metal or plastic foil, such as a blister pack. The pack or dispenser device may be accompanied by instructions for administration.

The appropriate and recommended dosages, formulation and routes of administration for treatment modalities such as chemotherapeutic agents, radiation therapy and biological/immunotherapeutic agents such as cytokines are known in the art and described in such literature as the *Physician's Desk Reference* (56$^{th}$ ed., 2002). In particular embodiments, the present invention comprises administering an anti-cancer agent such as any of those described below in Table 2, preferably for the treatment of breast, ovary, melanoma, prostate, colon or lung cancer, CML or soft tissue sarcomas, including but not limited to gastrointestinal stromal tumors as described below in section 5.11.

Because in certain embodiments, the methods of the invention comprise administration of sub-optimal amounts of the therapeutic modality, it is envisioned that the dosages of each therapeutic modality can be less than that used in standard therapy or known in the art.

In one embodiment, Gleevec™ is administered 50 mg to 100 mg, 100 mg to 200 mg, 200 mg to 300 mg, 300 mg to 400 mg, 400 mg to 500 mg, 500 mg to 600 mg, 600 mg to 700 mg, 700 mg to 800 mg, 800 mg to 900 mg, or 900 mg to 1000 mg daily. In certain embodiments, the total daily dose is administered to a subject as two daily doses of 25 mg to 50 mg, 50 mg to 100 mg, 100 mg to 200 mg, 200 mg to 300 mg, 300 mg to 400 mg, or 400 mg to 500 mg. Gleevec™ is administered orally in dosages of 100 mg to 1000 mg, preferably 200 mg to 900 mg, more preferably 300 mg to 800 mg, most preferably 400 mg to 600 mg. In a specific embodiment, Gleevec™ is administered orally, at a sub-optimal daily dosage. In preferred embodiments, the sub-optimal daily dosage of orally administered Gleevec™ is about 10 mg to 600 mg, about 50 mg to 400 mg, about 100 mg to 300 mg, or about 200 mg. In other embodiments, Gleevec™ is administered orally every other day, every third day, every fourth day, every fifth day, every sixth day, or once a week, at a dosage of 100 mg to 800 mg, 200 mg to 600 mg, 300 mg to 500 mg, or 400 mg.

TABLE 2

| Therapeutic Agent | | Dose/Administration/Formulation | |
|---|---|---|---|
| imatinib mesylate (Gleevec ™) | Oral (capsule) | 400-600 mg daily Capsules each contain imatinib mesylate equivalent to 100 mg imatinib free base | |
| doxorubicin hydrochloride (Adriamycin RDF ® and Adriamycin PFS ®) | Intravenous | 60-75 mg/m$^2$ on Day 1 | 21 day intervals |
| epirubicin hydrochloride (Ellence ™) | Intravenous | 100-120 mg/m$^2$ on Day 1 of each cycle or divided equally and given on Days 1-8 of the cycle | 3-4 week cycles |

TABLE 2-continued

| Therapeutic Agent | | Dose/Administration/Formulation | |
|---|---|---|---|
| fluorousacil | Intravenous | How supplied: 5 mL and 10 mL vials (containing 250 and 500 mg flourouracil respectively) | |
| docetaxel (Taxoter ®) | Intravenous | 60-100 mg/m² over 1 hour | Once every 3 weeks |
| paclitaxel (Taxol ®) | Intravenous | 175 mg/m² over 3 hours | Every 3 weeks for 4 courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | Intravenous or intramuscular injection | How supplied: 350 mg vial | Dosage is unclear from text. PDR 3610 |
| luprolide acetate (Lupron ®) | Single subcutaneous injection | 1 mg (0.2 mL or 20 unit mark) | Once a day |
| flutamide (Eulexin ®) | Oral (capsule) | 250 mg (capsules contain 125 mg flutamide each) | 3 times a day at 8 hour intervals (total daily dosage 750 mg) |
| nilutamide (Nilandron ®) | Oral (tablet) | 300 mg or 150 mg (tablets each contain 50 or 150 mg nilutamide) | 300 mg once a day for 30 days followed by 150 mg once a day |
| bicalutamide (Casodex ®) | Oral (tablet) | 50 mg (tablets each contain 50 mg bicalutamide) | Once a day |
| progesterone | Injection | USP in sesame oil 50 mg/mL | |
| ketoconazole (Nizoral ®) | Cream | 2% cream applied once or twice daily depending on symptoms | |
| prednisone | Oral (tablet) | Initial dosage may vary from 5 mg to 60 mg per day depending on the specific disease entity being treated | |
| estramustine phosphate sodium (Erncyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 mL of 20 mg/mL solution (100 mg) | |
| dacarbazine (DTIC-Dome ®) | Intravenous | 2-4.5 mg/kg | Once a day for 10 days. May be repeated at 4 week intervals |
| polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | |
| cisplatin | Injection | [n/a in PDR 861] How supplied: solution of 1 mg/mL in multi-dose vials of 50 mL and 100 mL | |
| mitomycin | Injection | supplied in 5 mg and 20 mg vials (containing 5 mg and 20 mg mitomycin) | |
| gemcitabine HCl (Gemzar ®) | Intravenous | For NSCLC-2 schedules have been investigated and the optimum schedule has not been determined 4 week schedule-administration intravenously at 1000 mg/m² over 30 minutes on 3 week schedule-Gemzer administered intravenously at 1250 mg/m² over 30 minutes | 4 week schedule-Days 1, 8 and 15 of each 28-day cycle. Cisplatin intravenously at 100 mg/m² on day 1 after the infusion of Gemzar. 3 week schedule-Days 1 and 8 of each 21 day cycle. Cisplatin at dosage of 100 mg/m² administered intravenously after administration of Gemzar on day 1. |
| carboplatin (Paraplatin ®) | Intravenous | Single agent therapy: 360 mg/m² I.V. on day 1 (infusion lasting 15 minutes or longer) Other dosage calculations: Combination therapy with | Every 4 weeks |

TABLE 2-continued

| Therapeutic Agent | Dose/Administration/Formulation | | |
|---|---|---|---|
| | | cyclophosphamide, Dose adjustment recommendations, Formula dosing, etc. | |
| ifosamide (Ifex ®) | Intravenous | 1.2 g/m² daily | 5 consecutive days Repeat every 3 weeks or after recovery from hematologic toxicity |
| topotecan hydrochloride (Hycamtin: ®) | Intravenous | 1.5 mg/m² by intravenous infusion over 30 minutes daily | 5 consecutive days, starting on day 1 of 21 day course |

5.8. Treatment and Prevention of Infectious Diseases

Infectious diseases that can be treated using the methods of the present invention are caused by infectious agents including, but not limited to, viruses, bacteria, fungi protozoa and parasites.

Infectious agents that can be treated according to the invention include, but are not limited to viruses, bacteria, fungi, and agents of protozoal disease.

Viral diseases that can be treated or prevented using the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial diseases that can be treated or prevented by use of the methods of the present invention are caused by bacteria including, but not limited to, mycobacteria *rickettsia, mycoplasma, neisseria, S. pneumonia, Borrelia burgdorferi* (Lyme disease), *Bacillus antracis* (anthrax), *tetanus, streptococcus, staphylococcus, mycobacterium, tetanus, pertissus, cholera, plague, diptheria, chlamydia, S. aureus* and *legionella*.

Protozoal diseases that can be treated or prevented by use of an immunoreactive reagent in conjunction with the methods of the present invention are caused by protozoa including, but not limited to, *leishmania, kokzidioa, trypanosoma* or *malaria*.

Parasitic diseases that can be treated or prevented by use of the methods of the present invention are caused by parasites including, but not limited to, *chlamydia* and *rickettsia*.

5.9. Treatment of Cancer

A number of non-vaccine cancer treatment modalities are currently in clinical trials and well-known in the art. The HSP/α2M preparation can be used in conjunction with such non-vaccine cancer treatment modalities for the treatment and prevention of the respective types of cancers. One skilled in the art would be able to determine experimental and standard anti-cancer therapies and treatments that could be used according to the methods of the present invention.

Cancers that can be treated using the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, acute lymphocytic leukemia, acute myelocytic leukemia, myeloblastic leukemia, promyelocytic leukemia, myelomonocytic leukemia, monocytic leukemia, erythroleukemia, chronic leukemia, chronic myeloid leukemia, chronic myelogenous leukemia, chronic myelocytic leukemia, chronic granulocytic leukemia, chronic lymphocytic leukemia, polycythemia vera, lymphoma, Hodgkin's disease lymphoma, non-Hodgkin's disease lymphoma, multiple myeloma, Waldenström's macroglobulinemia, heavy chain disease, soft tissue sarcomas, gastrointestinal stromal tumors, and glioblastomas.

6. EXAMPLE

Tumors Non-Responsive to Chemotherapy/Cytokine Treatment Respond after Administration of HSP-Peptide Complex Mice bearing tumors, such as LLC (D122) and B16, do not respond to treatment of Cyclophosphamide (Cy) in combination with interleukin-12 (IL-12). In a double-graft experiment, mice were injected with MCA207 (tumors known to respond to Cy+IL-12 treatment) and D122 at two opposite flanks, and tumors were allowed to grow to a significant size (10×10 mm), then the mice were treated with Cy+IL-12. The large MCA207 tumors regressed rapidly, whereas the D122 tumors continued to grow on the opposite flank of the same animals. The results demonstrated that certain tumors, e.g., D122 do not respond to Cy+IL-12 treatment, even though a vigorous response against another tumor is present in the same animal.

The tumors that responded to the treatment appear to be immunogenic, whereas other tumors that are non-responders were all poorly immunogenic. To test whether a host-derived immune recognition of the tumor in the forms of T cell priming prior to Cy+IL-12 treatment would result in the tumor responding to treatment, the following experiments were conducted. The following results demonstrated that if a mouse bearing a D122 tumor that does not respond to Cy+IL-12 treatment alone obtains immunological memory of the tumor, a tumor rejection will occur in the mice following treatment with Cy+IL-12.

Heat shock protein-peptide complexes were used for eliciting a robust T cell response that includes both CD4+ and CD8+ T cells in mice.

6.1. Materials and Methods

Naïve mice were either un-immunized, or immunized once at day 0 with 5 and 20 µg D122-derived gp96-peptide complexes administered subcutaneously, or 2 µg D122-derived gp96-peptide complexes administered intradermally. As a negative control, another group of mice were immunized with liver-derived gp96-peptide complexes. The D122-derived gp96-peptide complexes are HSP-peptide complexes endogenous to and isolated from D122 tumor cells. The liver-derived gp96-peptide complexes are HSP-peptide complexes endogenous to and isolated from liver cells. Two weeks after the immunization (day 14), the mice were challenged subcutaneously with 200,000 D122 cells. The immunization was sub-optimal for tumor rejection according to our previous experience and D122 tumors grew in all mice. When tumor size reached 10 mm or above in diameter (day 32-34), the mice were treated with Cy+IL-12 (Cy, 3 mg by intraparenteral administration; IL-12, 200 ng, intraparenteral administration for 5 days).

6.2. Results

| Mice immunized with | Cure rate (#/total) | Size of tumors cured (mm in diameter) |
|---|---|---|
| PBS | 2/16 | 7 and 10 |
| Liver-derived gp96-peptide complexes | 2/10 | 10 and 12 |
| D122-derived gp96-peptide complexes | 11/12 | From 8 to 22 |

As summarized in the table above, upon antigen-specific immunological stimulation with autologous tumor derived gp96-peptide complexes, non-responder tumor D122 became a responder to the treatment of Cy+IL-12. In groups un-immunized and immunized with liver-derived gp96-peptide complexes, only those mice bearing the smallest tumors (less than 10-12 mm in diameter) experienced tumor regression after Cy+1L-12 treatment. In contrast, in mice that were immunized with D122-derived gp96-peptide complexes, large D122 tumors such as those 22 mm in diameter, which are generally refractory to any kind of immunotherapeutic approaches reported, regressed completely after the Cy+1L-12 treatment. In addition, immunohistochemistry analysis for a number of tumor samples harvested from each group reveals that 1) No sign of T cell infiltration in the tumors removed from mice that were un-immunized or immunized with liver-derived gp96-peptide complexes before or after the Cy+IL-12 treatment; 2) In contrast, some T cell infiltration (both CD4+ and CD8+) was observed in tumors harvested from mice immunized with D122-derived gp96-peptide complexes 12 days, but not 6 days, after the Cy+IL-12 treatment was initiated.

7. EXAMPLE

Complete Elimination of Leukemia Cells in Patients in Chronic Phase CML after Administration of Combination Gleevec™ and HSP-Peptide Complex To test the feasibility of immunization with autologous tumor-derived hsp70-peptide complexes to treat patients in chronic phase CML, the following protocol was used (FIG. 1). The clinical protocol summarized in FIG. 1 includes all physical examinations, blood work, x-rays and bone marrows that were done before, during and after vaccination with an HSP preparation. Prior to inclusion in the study, subjects' diagnosis of CML was confirmed by bcr/abl molecular typing of peripheral blood or bone marrow obtained from the subject using polymerase chain reaction (PCR) to determine the presence or absence of bcr/abl chimeric proteins or transcripts.

7.1. Materials and Methods

Subjects that participated fulfilled the following criteria: subject displayed an Eastern Cooperative Oncology Group (ECOG) performance score less than 2; subject was at least 18 years of age, and capable of giving informed consent; less than one year has passed since the original diagnosis of Philadelphia chromosome positive CML in chronic phase; subject was not in cytogenetic remission; subject was not anticipating a bone marrow or stem cell transplant within the next six months unless such therapy was deemed necessary by a treatment physician due to evolution of the disease; subjects were allowed to maintain concurrent standard treatment hydroxyurea, Ara-C/day for 10 days or Gleevec™ (imatinib mesylate); subject lacked any serious illness such that medical condition might be compromised by participation in the study; subject showed adequate renal function as measured by serum creatinine levels less than 2.0, and adequate hepatic function, as measured by bilirubin and transaminase less than 2.0 times the upper normal limit; subject was not on corticosteroid therapy, or other immunosuppressive medication; and subject did not display a lack of anergy as shown by adequate delayed type hypersensitivity (DHT) response to at least 1 out of 3 antigens by skin testing with *Candida*, mumps and PPD, i.e., induration was greater than 0.5 cm 48 hours after placement.

Subjects were excluded if: subject displayed an ECOG performance score≥2; subject was more than 3 years out from original diagnosis of Philadelphia chromosome positive CML in chronic phase; subject was on IFN treatment; subject showed significant anemia, i.e., hemoglobin less than 10 g/dl or thrombocytopenia, i.e., platelet less than 20,000/µl, requiring transfusion; subject showed peripheral blast count over 10%; subject showed positive urine or blood pregnancy test; subject showed impaired renal function, i.e., serum creatine greater than or equal to 2.0, or impaired hepatic function, i.e., bilirubin or transaminase more than 2.0 times the upper normal limit; subject showed significant active infection requiring hospitalization at time of enrollment; subject with significant behavioral or psychological problems that prevented adequate follow-up.

A subject was discontinued for any of the following reasons: subject requested to withdraw for any reason; a proven effective therapeutic approach became available, and was preferred by the subject (e.g., the approval of other investigational medications by the regulatory agency, identification of an identical human leukocyte antigen (HLA) matched donor), the subject was lost to follow-up; the subject showed clear evidence of disease acceleration despite concurrent therapy as evidenced by the following signs and symptoms: peripheral blasts 10% or more; peripheral blast plus promyelocytes 30% or more; peripheral basophils 20% or more; thrombocytopenia less than 100,000/mm$^3$ unrelated to therapy; neutropenia less than 1,000/mm$^3$ unrelated to therapy; marrow blast 10% or more; significant marrow fibrosis; progressive splenomagly unresponsive to therapy; triad of WBC greater than 50,000/mm$^3$, hematocrit less than 25% and platelets less than 100,000/mm$^3$ not controlled with therapy; persistent unexplained fever; and cytogenetic clonal evolution; extramedullary disease with localized immature blast such as chloroma; any other reason which in the opinion of the investigator was to protect the best interest of the subject.

Prior to administration of their first HSP preparation, subjects had been receiving Gleevec™ therapy (400-800 mg daily in capsule form, 400-600 mg daily doses administered once a day, or 800 mg in two daily doses of 400 mg each) for 2 days, 5 months, 9 months, 10 months, and 1 year, respectively. Subjects satisfying the above criteria were allowed to remain on Gleevec™ therapy throughout the study. Subjects subsequently underwent aphaeresis using peripheral vein access to collect peripheral mononuclear cells. The majority of the specimen was used for the purification of hsp70-peptide complexes. The autologous hsp70-peptide complexes were then purified using an ADP-agarose protocol, substantially as described in Section 5.3.1 above. A small fraction of the collection was used as targets for a CTL assay. Subjects received an intradermal injection of 50 μg hsp70-peptide complexes in the skin of the forearm weekly over a two month period for a total of 8 injections, in addition to Gleevec™ therapy (400-800 mg daily in capsule form, 400-600 mg daily doses administered once a day, 800 mg doses administered twice a day). Blood samples were drawn three times to access the status of the immune system. Blood was collected prior to the vaccination, during the vaccination and 1-2 weeks after the 8th vaccination (see FIG. 1). At the end of the treatment, all subjects underwent full hematological and cytogenetic staging on the bone marrow (see Silver et al., 1999, Blood 94(5):1517-1536).

In addition, to collect feasibility and toxicity data, the development of anti-tumor immunity was measured according to methods known in the art, such as: (1) an increase in peripheral blood of IFN-γ producing CD8+ T-lymphocytes which are reactive to the autologous bcr/abl positive peripheral mononuclear cells (see e.g., Janetzki et al., 2000, Int. J. Cancer 88:232-238); (2) an increase of PR-1 specific CTLs by PR1-HLA-A2 tetramer techniques in patients who are HLA-A2 positive (see e.g., Clark et al., 2001, Blood 98(10): 2887-2893 and Molldrem et al., 1999, Cancer Research 59: 2675-2681); (3) the change of immunophenotype of peripheral lymphocytes (see e.g., Akel et al., 2002, Clin. Lab. Haem. 24:362-367); and (4) the cytogenetic remission of Philadelphia chromosome from the bone marrow (see e.g., Wang et al., 2002, British J. Haematology 118:771-777).

Combined treatment in the five evaluable subjects resulted in complete elimination of leukemia cells as determined by: RT-PCR analysis determining the presence or absence of bcr/abl transcripts in the peripheral blood or bone marrow collected from treated patients, (see e.g., Merx et al., 2002, Leukemia 16:1579-1583; Wang et al., 2002, British Journal of Haematology 118: 771-777; and Stentoft et al., 2001, Eur. J. Haemotol. 67: 302-308); cytogenetic response, one of the criteria used in the approval of Gleevec™ (see Silver et al., 1999, Blood 94(5):1517-1536); or a combination of RT-PCR and cytogenetic response. Based on previous reports, less than 10 percent of patients treated with Gleevec™ alone achieve responses using these same criteria. See Druker et al., 2002, Hematology (Am. Soc. Hematol. Educ. Program): 111-135, at 114-115.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method of treating a cancer in a subject in need thereof, the method comprising:
administering to the subject Bevacizumab, wherein the subject is a candidate for receiving Bevacizumab to treat the cancer, and wherein the subject has been administered a purified heat shock protein preparation comprising a heat shock protein-peptide complex comprising a heat shock protein covalently or noncovalently attached to an antigenic peptide, wherein the antigenic peptide displays antigenicity of an antigen of the cancer.

2. The method of claim 1, wherein the purified heat shock protein preparation comprises heat shock protein-peptide complexes that comprise one or more of hsp70, hsp90, hsp110, gp96, grp170, and calreticulin.

3. The method of claim 2, wherein the purified heat shock protein preparation comprises heat shock protein-peptide complexes that comprise gp96.

4. The method of claim 1, wherein the subject receives further administrations of Bevacizumab and the purified heat shock protein preparation, wherein the administrations are repeated for up to 12 cycles.

5. The method of claim 1, wherein the subject is administered the purified heat shock protein preparation once a week for the first 4 weeks after an initial administration of the purified heat shock protein preparation.

6. The method of claim 5, wherein the subject is administered the purified heat shock protein preparation once every other week after the first 4 weeks of administration of the purified heat shock protein preparation.

7. The method of claim 1 further comprising administering to the subject radiation therapy.

8. The method of claim 1, wherein the Bevacizumab is administered for a first period of time, followed by a further administration of the purified heat shock protein preparation for a second period of time, wherein this sequential administration is repeated.

9. The method of claim 1, wherein Bevacizumab is administered concurrently with further administrations of the purified heat shock protein preparation.

10. The method of claim 1, wherein the Bevacizumab is cyclically administered with purified heat shock protein preparation.

11. The method of claim 1, wherein the purified heat shock protein preparation is autologous to the subject.

12. The method of claim 1, wherein the subject is human.

13. The method of claim 12, wherein the purified heat shock protein preparation comprises heat shock protein-peptide complexes isolated from cells of the cancer.

14. The method of claim 1, wherein the purified heat shock protein preparation comprises heat shock protein-peptide complexes comprising heat shock proteins non-covalently attached to antigenic peptides.

15. The method of claim 1, wherein the antigenic peptide displays antigenicity of a tumor-specific antigen or a tumor-associated antigen of the cancer.

16. The method of claim 1, wherein the cancer is a relapse form of cancer.

17. The method of claim 16, wherein the subject is human and wherein the antigenic peptide displays antigenicity of a tumor-specific antigen or a tumor-associated antigen of the cancer.

18. The method of claim 1, wherein the Bevacizumab is administered intravenously.

19. The method of claim 18, wherein the purified heat shock protein preparation is administered intradermally.

20. The method of claim 1, wherein the purified heat shock protein preparation is administered intradermally.

\* \* \* \* \*